US005476926A

United States Patent [19]
Spiegelman et al.

[11] Patent Number: 5,476,926
[45] Date of Patent: Dec. 19, 1995

[54] ADIPOCYTE-SPECIFIC DNA SEQUENCES AND USE THEREOF IN THE PRODUCTION OF TRANSGENIC ANIMALS EXHIBITING ALTERED FAT TISSUE METABOLISM

[76] Inventors: Bruce M. Spiegelman, 271 Waban Ave., Waban, Mass. 02168; Reed Graves, 122 Riverway, Apt. 3, Boston, Mass. 02215; Susan Ross, 2151 W. Caton, Chicago, Ill. 60647

[21] Appl. No.: 771,022

[22] Filed: Oct. 7, 1991

Related U.S. Application Data

[63] Continuation-in-part of Ser. No. 589,971, Sep. 28, 1990, abandoned.

[51] Int. Cl.$^6$ .......................... C12N 15/11; C07H 21/04
[52] U.S. Cl. .................. 536/24.1; 536/23.1; 435/320.1; 935/36
[58] Field of Search ...................... 435/69.1; 536/24.1, 536/23.1; 935/36

[56] References Cited

U.S. PATENT DOCUMENTS

| | | | |
|---|---|---|---|
| 4,736,866 | 4/1988 | Leder et al. | 800/2 |
| 4,870,009 | 9/1989 | Evans et al. | 435/69.4 |
| 4,873,316 | 10/1989 | Meade et al. | 530/412 |

OTHER PUBLICATIONS

Platt et al. Proc. Nat. Acad. Sci., USA 86 7490–7494 (1989).
Min et al. Nucleic Acids Res. 14 8879–8892 (1986).
Phillips et al. J. Biol. Chem. 261 10821–10827.
Hresko et al. Proc. Nat. Acad. Sci., USA 85 8835–8839 (1988).
Hunt et al. Proc. Nat. Acad. Sci., USA 83 3786–3790 (1986).
Hanahan Science 246:1265–1275 (1989).
van Zonneveld et al. Proc. Nat. Acad. Sci., USA, 85 5525–5529 (1988).
Bernlohr et al., "Expression of specific mRNAs during adipose differentiation: Identification of an mRNA encoding a homologue of myelin P2 protein", Proc. Natl. Acad. Sci., U.S.A., 81:5468–5472 (Sep. 1984).
Zezulak and Green, Molecular and Cellular Biology, vol. 5, No. 2, 419–421 (Feb. 1985).
Cook et al., The Journal of Cell Biology, 100:514–520 (Feb. 1985).
Bernlohr et al., The Journal of Biological Chemistry, vol. 260, No. 9, 5563–5567 (May, 1985).
Phillips and Green, The Journal of Biological Chemistry, vol. 261, No. 3, 10821–10827 (Aug. 1986).
Distel et al., Cell, 49:835–844 (Jun., 1987).
Cook et al., Proc. Natl. Acad. Sci., USA, 85:2949–2953 (May, 1988).
Gaskins et al., J. Anim. Sci., 67:2263–2272 (1989).
Yang et al., Proc. Natl. Acad. Sci., USA, 86:3629–3633 (May, 1989).
Herrera, Molecular and Cellular Biology, vol. 9, No. 12, 5331–5339 (Dec. 1989).
Christy et al., Genes and Development, 3:1323–1335 (1989).
Wilkison et al., The Journal of Biological Chemistry, 265:477–482 (1990).
Cundiff, "The Application of Genetic Principles and Genetic Engineering to Improve Efficiency of Lean Meat Production", Reciprocal Meat Conference Proceedings, (1983).
Pursel et al., "Gene Transfer for Enhanced Growth of Livestock", Animal Growth Regulation, Chapter 16.
Fox et al., "Metatastic Hibernomas in Transgenic Mice Expressing an a–Amylase–SV40 Antigen Hybrid Gene", Science, 244:460–463 (Apr., 1989).
Hammer et al., "Use of Gene Transfer to Increase Animal Growth", Quantitative Biology, (Cold Spring Harbor Symposium) 50:379–387 (1985).
Hammer et al., "Genetic Engineering of Mammalian Embryos", J. Anim. Sci., 63:269–278 (1986).
Miller et al., "Expression of human or bovine growth hormone gene . . . ", J. of Endocrinology, 120:481–488 (1989).
Pursel et al., "Development of 1–cell and 2–cell pig ova after microinjection of genes", J. Anim. Sci., 65:402 (1987 Supp.).
Bolt et al., "Transgenic swine transmit foreign gene to progeny", J. Anim. Sci., 63:203 (1986 Supp.).
Pursel et al., "Genetic Engineering of Livestock", Science, 244:1281–1288 (Jun. 1986).
Richardson et al., "Transforming Growth Factor Type B (TGF–B) And Adipogenesis In Pigs", J. Anim. Sci., 67:2171–2180 (1989).
Sinnett–Smith and Woolliams, "Antilipogenic But Not Lipolytic Effects of Recombinant DNA–Derived Bovine Somatotropin Treatment . . . ", Int. J. Biochem., 21:535–540 (1989).
Navre and Ringold, "Differential Effects of Fibroblast Growth Factor . . . ", The Journal of Cell Biology, 109:1857–1863 (Oct. 1989).
Rexroad et al., "Gene insertion: Role and limitations of technique in farm animals as a key to growth", Invited Papers for May 3–7, 1987 Symposium at Beltsville Agricultural Research Center.
Hausman et al., "Endrocrine Regulation of Adipogenesis," Animal Growth Regulation (Campion et al., ed. 1989).
Beerman, "Status of Current Strategies for Growth Regulation", Animal Growth Regulation, (Campion et al., ed. 1989).

Primary Examiner—Robert A. Wax
Assistant Examiner—Gabriele E. Bugaisky
Attorney, Agent, or Firm—Julia D. Hart

[57] ABSTRACT

Regulatory DNA sequences are provided, which are obtained from the 5' flanking region of genes which are expressed primarily in differentiated adipose tissue. These DNA sequences are largely responsible for driving the expression of endogenous genes specifically in adipose tissue in vivo. The DNA sequences can be located in a region 5' of the gene, distinct from promoter sequences which provide a site for the initiation of transcription into DNA, or can be located within the region of the promoter itself.

When operatively linked to a gene encoding a recombinant protein capable of exerting an effect on the metabolism of adipocytes, the DNA sequences of the invention can be used to produce transgenic animals which exhibit altered fat tissue metabolism. Depending upon the nature of the gene introduced in the animal or ancestor thereof at an embryonic stage, the transgenic animals are leaner or more obese than non-transgenic animals of the same species.

7 Claims, 17 Drawing Sheets

ARE2      5'-GCAGGAAGTCACCACCCAGAGAGCA-3'

ARE4      5'-TGGAAGTGTCACAGCCCAAACACTC-3'

ARE2 M1   5'-GCAGGAAGTGTAAGCCCAGAGAGCA-3'

Fig. 12

ARE6      5'-ATTTCAC CCAGA GAAGG GATTGA-3'

ARE7      5'-CTCTGAT CCAGT AAGAAGG CAAATG-3'

ARE6 M1   5'-ATTTCAC CCATCT AGAAGG GATTGA-3'

ARE6 M2   5'-ATTTC CTG CAGA GAAGG GATTGA-3'

ADIPOCYTE-SPECIFIC DNA SEQUENCES AND USE THEREOF IN THE PRODUCTION OF TRANSGENIC ANIMALS EXHIBITING ALTERED FAT TISSUE METABOLISM

This invention was made with Government support under National Institutes of Health Grant DK31405. The Government therefore has certain rights in this invention. This application is a continuation-in-part of U.S. Ser. No. 07/589,971, filed on Sep. 28, 1990 now abandoned.

FIELD OF INVENTION

This invention relates to adipocyte-specific DNA sequences capable of directing expression of recombinant proteins specifically in adipose tissue in vivo, to an expression system which comprises the adipose-specific DNA sequence operatively linked to DNA sequences coding for a protein capable of exerting an effect on adipose tissue metabolism, and also relates to the use of the expression system in the production of transgenic animals which exhibit altered fat tissue metabolism. When the expression system is transgenically incorporated in an animal, the recombinant protein is expressed primarily in adipose tissue. The transgenic animals are either lean or obese compared to non-transgenic animals of the same species, depending upon the nature of the DNA sequence operatively linked to the adipocyte-specific DNA sequence.

The invention also relates to trans-acting nuclear factors found in differentiated adipocyte, but not in preadipocyte, nuclear extracts that bind to shorter sequences within adipocyte-specific enhancer elements. Differentiation-dependent expression of the gene under the control of the enhancer element can be blocked by interfering with the binding of the nuclear factor to the cognate sequences, thereby providing a potential therapeutic modality for adipose tissue disorders such as obesity.

BACKGROUND OF INVENTION

Transgenic animals carry a gene which has been introduced into the germ line of an animal or an ancestor of the animal at an early stage in development. Wagner et al., *Proc. Natl. Acad. Sci. USA*, 78:5016 (1982). The ability to introduce new genes into the germ line of animals and thereby produce proteins outside of their normal environment and separated from their usual physiological control mechanisms has been extremely valuable for studying various aspects of gene expression. The technology also presents significant potential for improving various traits in animals, such as resistance to disease, reproductive rates and growth and lactation.

Much of the work involving transgens expression in animals has utilized the mouse as the experimental animal. For example, U.S. Pat. No. 4,736,866, describes the generation of transgenic mice whose germ line cells and somatic cells carry an activated oncogene sequence introduced into the animal or the ancestor of the animal at a germ line stage. Numerous other genes have been introduced into mice in an effort to gain a better understanding of gene expression in animals. See, for example, a review by Brinster and Palmiter, *Harvery Lectures*, 80:1–38 (1986) and Palmiter and Brinster, *Annual Review of Genetics*, 20:465–499 (1986).

More recently, gene transfer has been extended to domestic animals, including pigs, chickens, fish, cattle, rabbits and sheep. Pursel et al., *Science*, 244:1281–88 (1989). Many of the experiments in commercially important livestock have been designed to test the feasibility of introducing foreign growth promoting genes into the germ line of the livestock and thereby enhance growth performance. One approach that has received a great deal of attention is the introduction of growth regulating genes under the control of heterologous promoters into the germ line of the livestock, to allow long term production of the peptides in ectopic tissue.

The first attempt at applying the technology to domestic animals involved the introduction of a fusion gene including the mouse metallothionein (MT) regulatory/promoter sequence fused to the human growth hormone gene into the genome of pigs. Hammer et al., *Nature*, 315:380 (1985); Brem, *Zuchygiene*, 20:251 (1985). Since that time, several other growth promoting genes, including rat, ovine and bovine growth hormone, human growth releasing-factor and bovine insulin-like growth factor have been introduced into the germ lines of a variety of domestic animals. Most of the transferred genes in commercially important livestock have been under the control of the mouse MT promoter.

The foregoing strategy has resulted in the stimulation of growth and enhancement of conversion of food to protein in pigs, Pursel et al., *Science*, 244:1281 (1989), which indicates that an important practical utility for the technology exists. Unfortunately, the procedures heretofore employed have also resulted in detrimental side effects on the general health of the transgenic animals. Id.

In addition to the demand for improved rate and efficiency of body weight gain in commercially important livestock, there is also a strong demand in the agricultural industry for altered meat composition toward a leaner, less fat product consistent with medical advice that human beings reduce their consumption of animal fat. Although a side effect of the growth enhancing experimentation in transgenic animals has been a reduction in subcutaneous fat, the other deleterious side effects associated with the technology indicate that the prior technology is not a viable technique for providing leaner transgenic livestock. Other current strategies for growth regulation, including a shift toward leaner animals, include implantation or oral administration of natural or synthetic steroids, injection of exogenous somatotropin (growth hormone) or growth hormone releasing factor, oral or parenteral administration of B-adrenergic agonists and immunoneutralization. For a review, see Beerman, *Status of Current Strategies For Growth Regulation* in ANIMAL GROWTH REGULATION, 377 (1989).

While various of these techniques have been successfully utilized to reduce carcass fat in animals, each involves the routine administration of the factors to individual animals and does not result in alteration of the germ line to provide a continuous source of leaner animals. Moreover, hormonal treatments have an effect on many tissues, not just the tissue whose composition is to be altered. Alternative approaches for use of gene manipulation to alter body composition toward less fat tissue are therefore indicated.

One of the advances that would significantly increase the likelihood of success of producing leaner strains of transgenic animals would be to place the genetic material under the control of a promoter or enhancer sequence specific for fat (adipose) tissue. Use of such a tissue specific control element should result in expression of the genes only in the tissue whose composition is to be altered. Such an adipocyte-specific control element could be used, not only in the agricultural industry to produce animals with reduced fat content, but could also be utilized to alter fat metabolism in experimental animals. As an example, the fat-specific element could be used to alter the levels of endogenous genes that are thought to play key roles in the functioning of adipocytes, thereby allowing a better understanding of their roles in both adipose homeostasis and in disease states involving this tissue. The element could also be utilized in the development of small, organic pharmaceutical molecules which interfere with the binding of the protein factor to the adipose specific regulatory element, to thereby control transcription in a manner designed to combat regulatory defects associated with the disease state in fat tissue.

Prior research efforts have been directed to the elucidation of promoter/regulator sequences responsible for the expression of various proteins expressed primarily in adipocytes (fat-filled cells). For example, the promoter of the aP2 gene has been isolated and used as a model for the study of differentiation- and hormonally-linked gene regulation (Hunt et al., *Proc. Natl. Acad. Sci. USA*, 83:3786– 3790 (1986); Phillips et al., *J. Biol. Chem.*, 261: 10821– 10827 (1986); Cook et al., *Proc. Natl. Acad. Sci. USA*, 85:2949–2953 (1988). AP2 is a novel gene product which is transcriptionally activated during adipocyte differentiation and is a member of the lipid-binding protein family.) Sequences from the aP2 proximal promoter (−247 or −168 to +21) have been shown to direct differentiation-dependent expression of the bacterial chloramphenicol acetyltransferase (CAT) upon transient transfection into preadipocytes and adipocytes (Distel et al., *Cell*, 49:835–844 (1987); Yang et al., *Proc. Natl. Acad. Sci. USA*, 86:3629–3633 (1989); Cook et al., *Proc. Natl. Acad. Sci. USA*, 85:2949–2953 (1988); Christy et al., *Proc. Natl. Acad. Sci. USA*, 86:3629–3633 (1989)) and several regulatory elements that strongly influence this expression have been identified. These include an AP-1 site at −120, where a sequence-specific interaction between Fos-containing protein complexes and DNA was first demonstrated (Distel et al., *Cell*, 49:835–844 (1987); Rauscher et al., *Cell*, 52:471–480 (1988)). An additional positive-acting element at position −140 was shown to bind the transcription factor C/EBP in extracts from adipose cells and a distinct protein from preadipocyte extracts (Christy et al., *Proc. Natl. Acad. Sci. USA*, 86:3629–3633 (1989); Herrera et al., *Mol. Cell Biol.*, 9:5331– 5339 (1989). Both the AP-1 and C/EBP binding sites have been shown to function positively in adipose cells and the AP-1 site is required for response of this promoter to cyclic AMP analogues (Herrera et al., *Mol. Cell Biol.*, 9:5331–5339 (1989); Christy et al., *Proc. Natl. Acad. Sci. USA*, 86:3629–3633 (1989).

The promoter for the adipose-specific gene product, adipsin, has also been studied in some detail.

None of these sequences have heretofore been shown to direct expression of genetic material in fat tissue in the animal. The current inability to direct expression directly to adipose tissue in vivo continues to be a major problem that has hampered the use of transgenic technology to regulate the fat metabolism of domestic animals.

Accordingly, it is an object of the present invention to provide DNA sequences capable of directing the expression of recombinant proteins specifically in adipose tissue in vivo.

Another object of the present invention is to provide an expression system comprising the adipose-specific DNA sequence operatively linked to a DNA sequence coding for a protein capable of altering adipose tissue metabolism.

Another object of the present invention is to provide transgenic animals exhibiting altered fat tissue metabolism that can be used as animal models in the study of adipose homeostasis and disease states associated with fat tissue.

A still further object of the present invention is to provide transgenic livestock with decreased adipose tissue content which are leaner than non-transgenic animals of the same species.

Yet another object of the invention is to identify DNA sequences which, upon binding of a trans-acting protein factor, are primarily responsible for adipose differentiation-dependent expression of the gene.

SUMMARY OF THE INVENTION

These as well as other objects and advantages are achieved in accordance with the present invention which provides regulatory DNA sequences isolated from the 5' flanking region of genes which are expressed primarily in differentiated adipose tissue. These regulatory DNA sequences are primarily responsible for driving the expression of endogenous genes specifically in adipose tissue in vivo. The regulatory sequences can be located in a region 5' of the gene, distinct from promoter sequences which provide a site for the initiation of transcription into mRNA, or can be located within the region of the promoter itself.

According to this invention, the adipose-specific DNA sequences are operatively linked to a DNA sequence coding for a recombinant protein capable of exerting an effect on the metabolism of adipocytes, and the thus-obtained expression system used to produce transgenic animals which exhibit altered fat metabolism. Depending upon the nature of the DNA sequence introduced in the animal or ancestor thereof at an embryonic stage, the transgenic animals are leaner or more obese than non-transgenic animals of the same species.

Since the regulatory sequences employed in the generation of the transgenic animals of the invention are adipose-specific, the genes are expressed in adipose tissue, and expressed minimally, if at all, in other tissues, thereby reducing the potential for deleterious effects associated with non-tissue specific promoter/regulators. When a DNA sequence coding for a recombinant protein having a lipolytic or lipogenic effect on adipose tissue is introduced into the germ line of an animal, such as a mouse, under the control of an adipose-specific DNA sequence of the present invention, leaner or more obese animals, respectively, can be produced. Such animals are useful as models in the study of adipose homeostasis and the disease state associated with adipose tissue. When a DNA sequence coding for a protein having a lipolytic or anti-lipogenic effect on adipose tissue is introduced under the control of the adipose-specific element into the germ line of commercially important livestock, leaner strains of livestock can be produced.

BRIEF DESCRIPTION OF THE DRAWING

FIG. 2A comprises two chromatographs from CAT assays from two independently generated stains of 247aP2CAT transgenic mice, 247aP2CAT $2_1$ and 247aP2CAT $3_1$a.

Figure 2A:
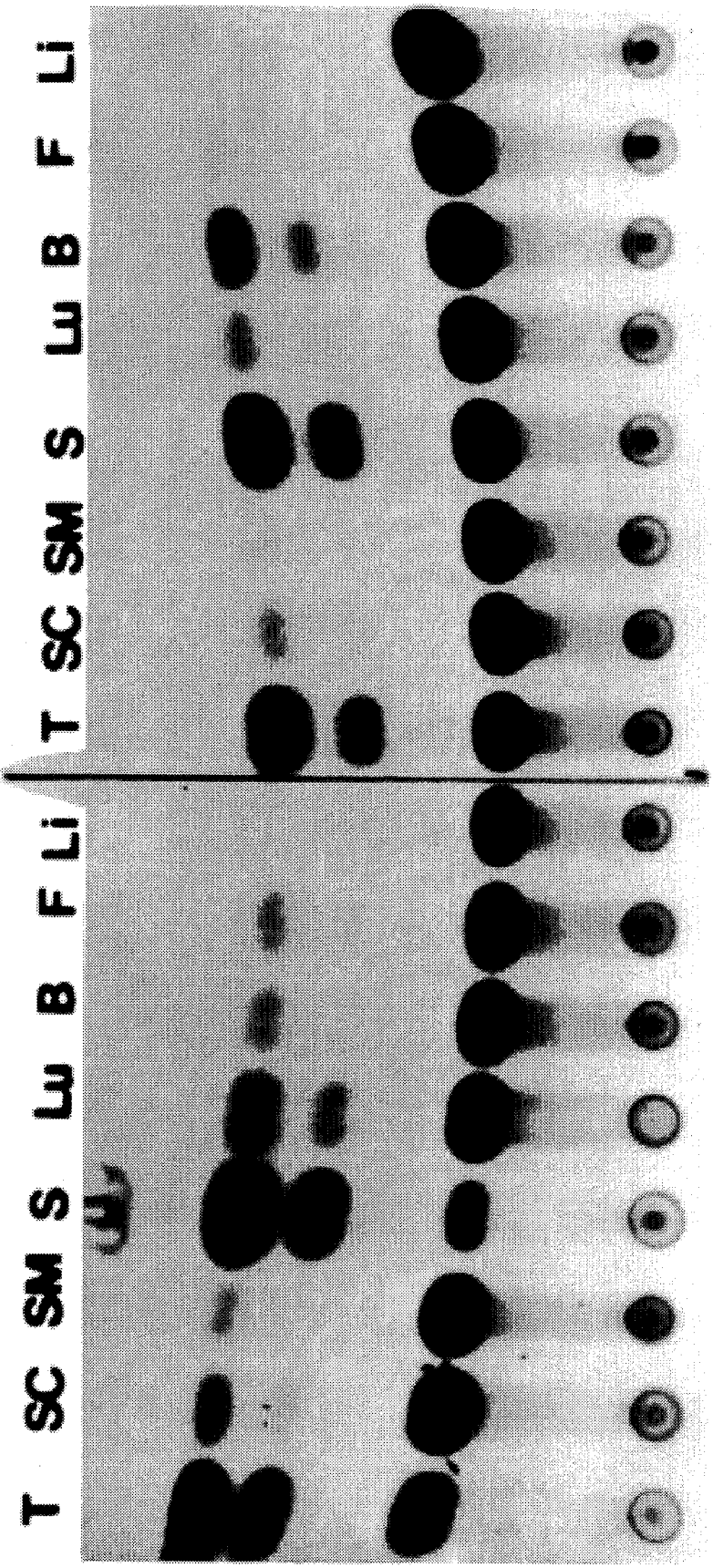
Figure 2B:
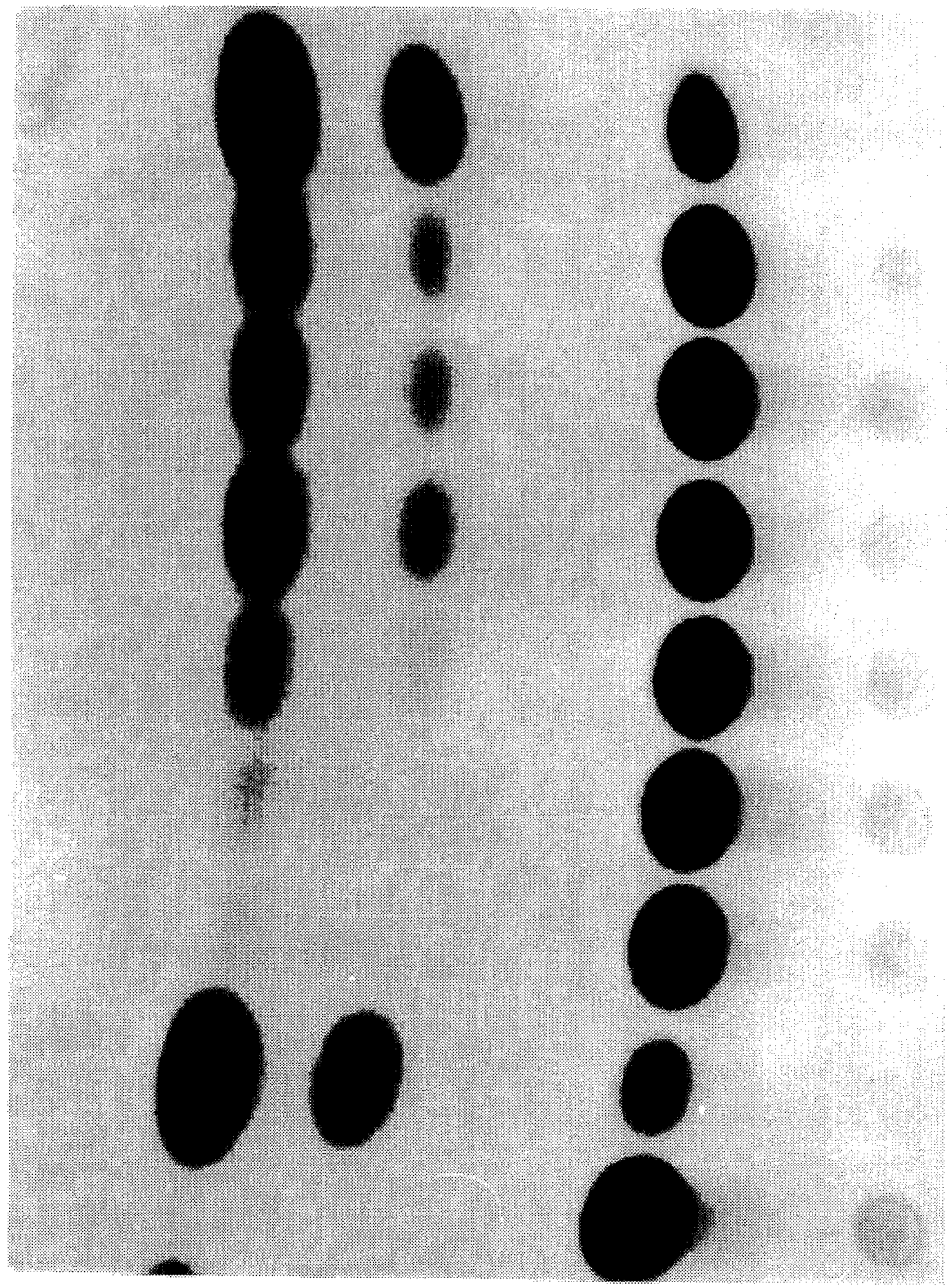
FIG. 2B is a chromatograph from the CAT assay from the 5.4aP2CAT 25 transgenic mouse.

The abbreviations used in FIGS. 2A and 2B are: T, thymus; SC, spinal cord; SM, skeletal muscle; S, spleen; Lu, lung; B, brain; F, fat; Li, liver; SG, salivary gland; BF, brown fat; H, heart.

Figure 3:
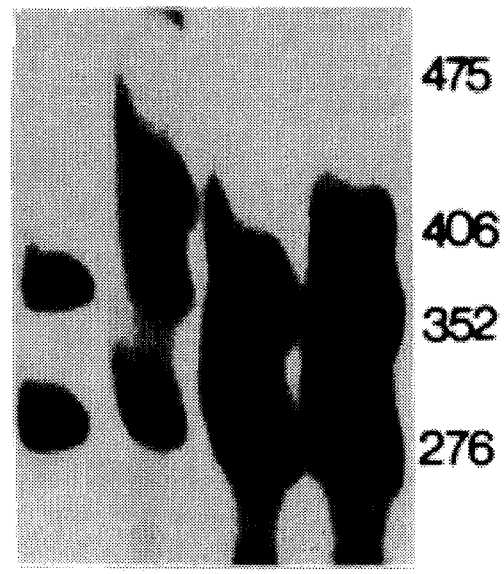
Figure 3:
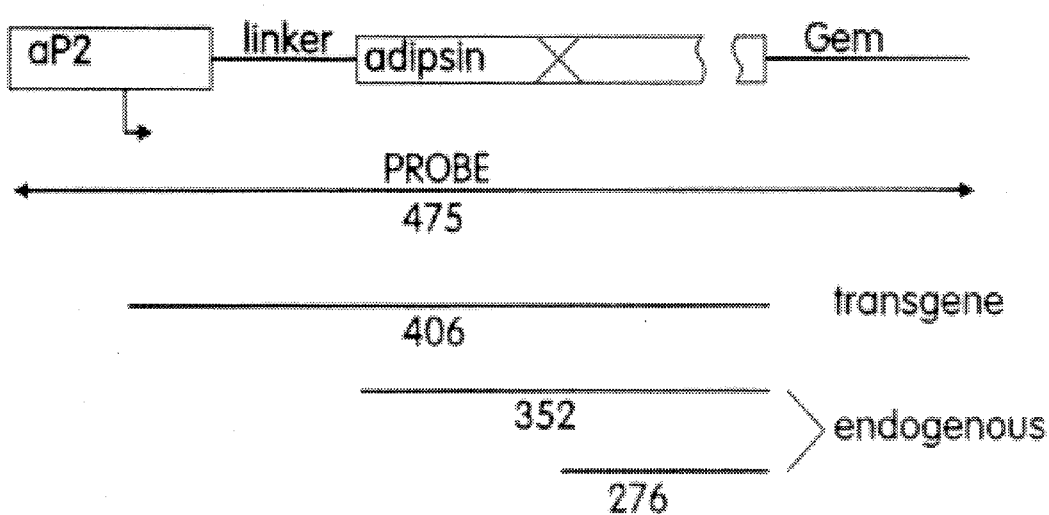

FIG. 3 is a chromatograph illustrating the results of the RNAase protection assay of RNA isolated from the tissues of 5.4aP2and transgenic and non-transgenic control mice. A 430 bp fragment from the junction between the aP2 and adipsin sequences was cloned into the Bluescript vector and used to make the 475 bp probe. The X within the adipsin sequence represents an alternative splice site not present in the cDNA that is utilized in approximately 50% of the endogenous adipsin transcripts. A fragment of 406 nt is protected from the transcripts initiated in the aP2 sequences in the transgene, while the endogenous transcripts protect fragments of 352 nt and 276 nt. Abbreviations utilized are N, non-transgenic; T, transgenic; S, spleen; BF, brown fat; F, fat.

Figure 4:
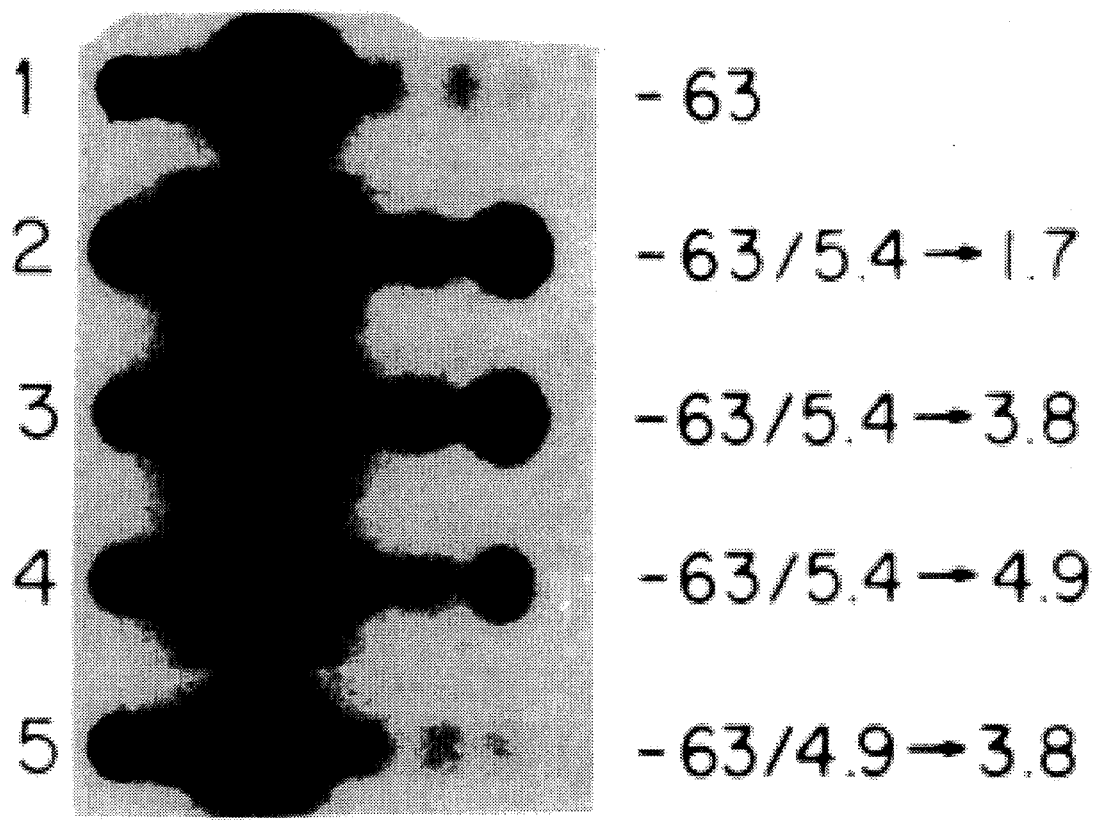

FIG. 4 illustrates the results of the CAT assays performed on extracts from 3T3-F442A adipocytes transiently transfected with 20 µg of plasmid DNA, wherein the plasmids were a series of deletion constructs of −5.4 to −1.7 aP2CAT. The origin and orientation of the DNA fragments inserted at the Hind III site of the basal −63aP2CAT vector is indicated above each lane (e.g. −63/5.4–1.7 has the −5.4 sequence fused to the −63 sequence and the −1.7 kb sequence at the 5' end of the construct) −63 is the basal vector alone.

Figure 5:
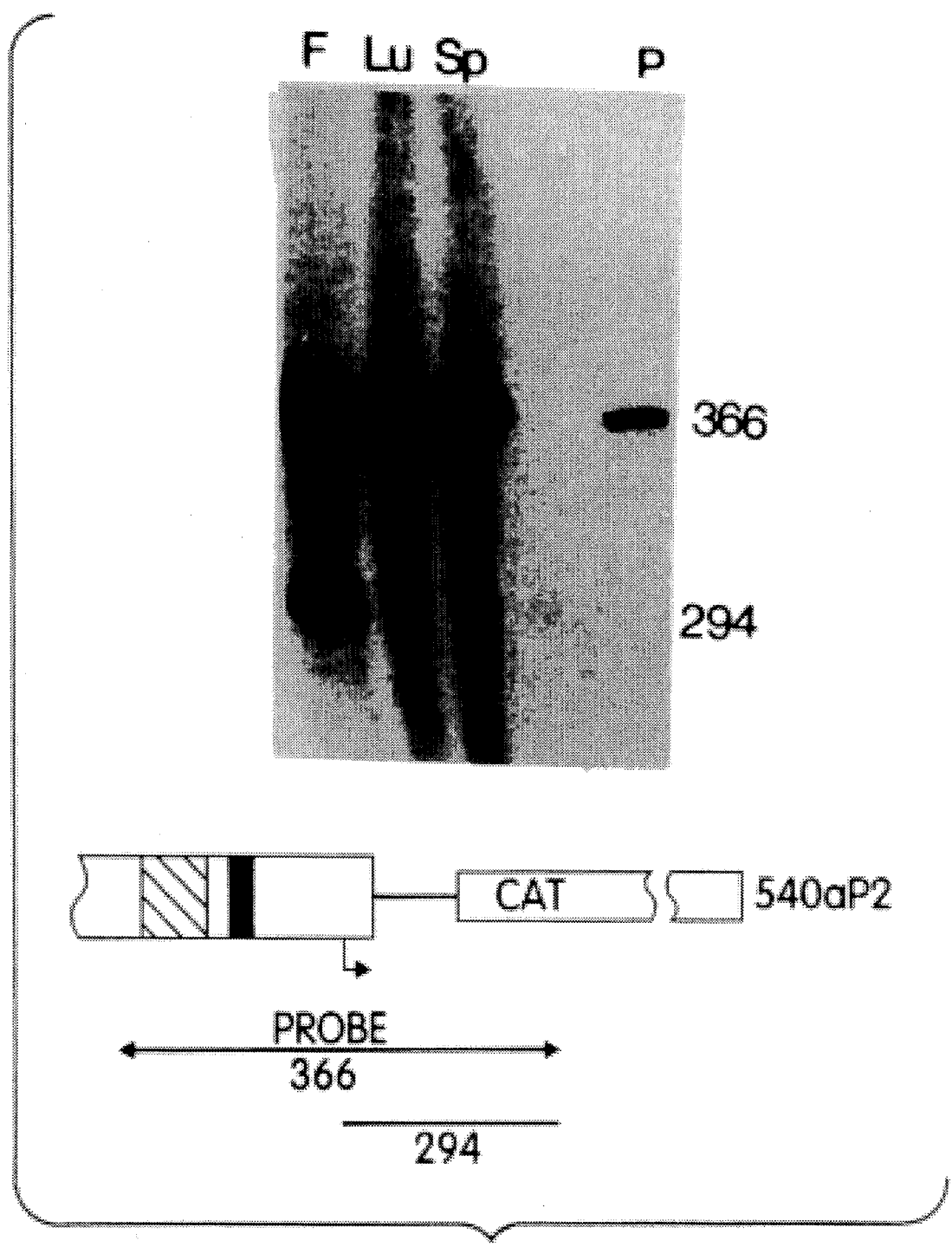

FIG. 5 illustrates the results of the RNAase T1 protection assay of RNA isolated from the tissues of a 518aP2CAT 2 transgenic mouse. A fragment spanning the junction between the aP2 promoter and the CAT sequence 5' from 518aP2CAT DNA was subcloned into a Gemini vector and used to make the probe of 366 nt. Transcripts initiating from the aP2 sequences in the 518aP2CAT transgene protect a fragment of 294 nucleotides. The abbreviations used are: F, fat; Lu, lung; Sp, spleen; and P, probe.

Figure 6:
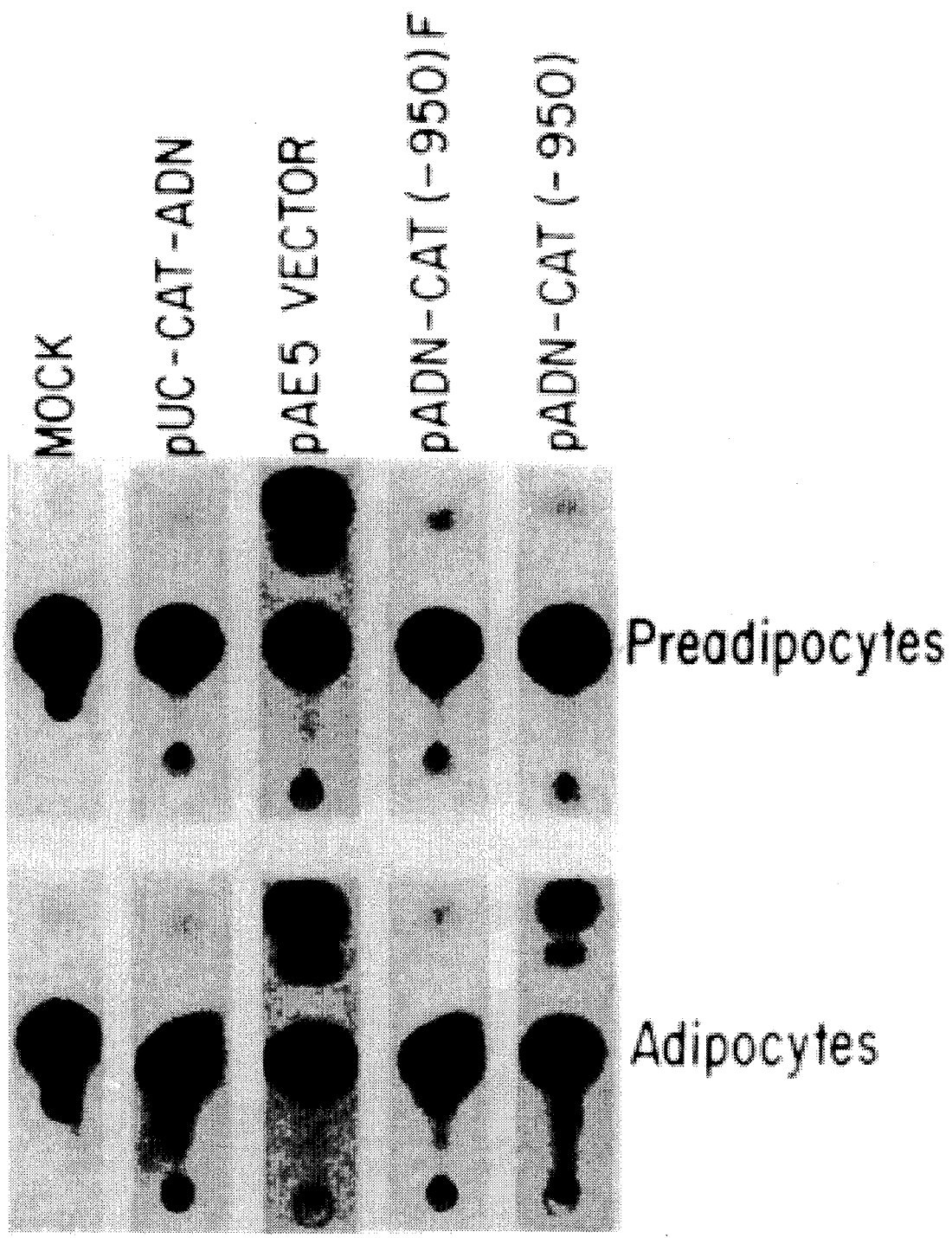

FIG. 6 is a chromatograph illustrating the differentiation-dependent gene expression from the adipsin promoter DNA. Transfections were done with 10 µg of each plasmid. Mock transfections included DEAE-dextran but no DNA. The pUCCAT-AND plasmid contained adipsin sequences from −950 to +35 placed 5' to the CAT gene and no exogenous enhancer sequences. The pAE5 vector contained SV40 promoter sequences upstream of CAT and Akv enhancer sequences in the 3' position relative to the CAT gene. In pADN-CAT (−950)F, adipsin sequences −950 to +35 are in an inverted orientation relative to the CAT gene; in pADN-CAT (−950), the adipsin sequences are in the proper 5' to 3' orientation.

Figure 7:
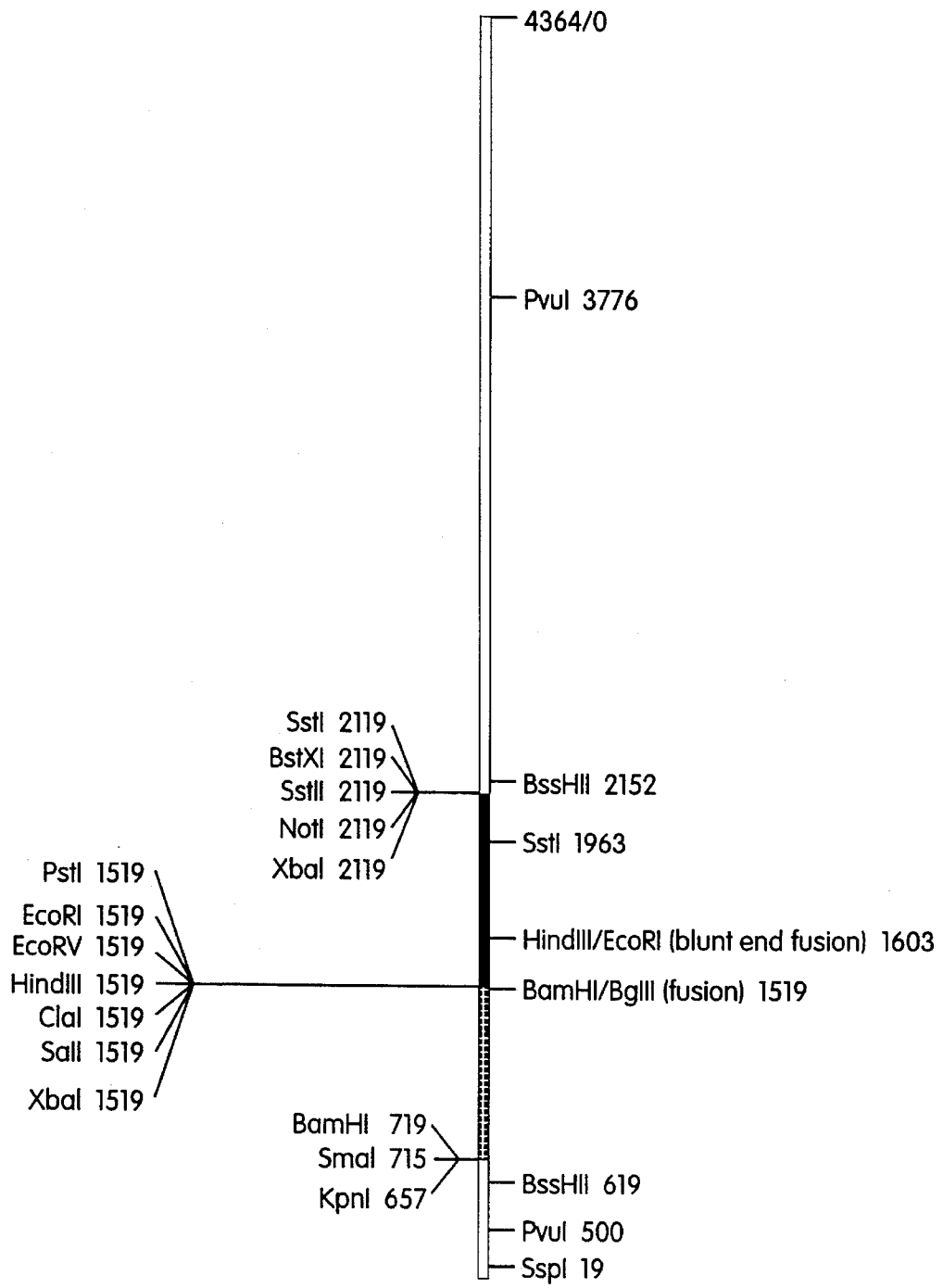

FIG. 7 is a schematic map of the TAP vector described in Example 6. In the figure, the aP2 promoter is shown as the closed bar; the PstI site (1519) is +21; the HindIII/EcoRI sites (1603) is −63 fused to −5.4 kb; and the XbaI site (2119) is −4.9 kb. The open bar represents the sequence from the BluescriptII+ vector; the hatched bar is from SV40 and contains the small t splice and polyadenylation signals; the closed bar is from aP2 promoter. Coordinates are approximate.

Figure 8:
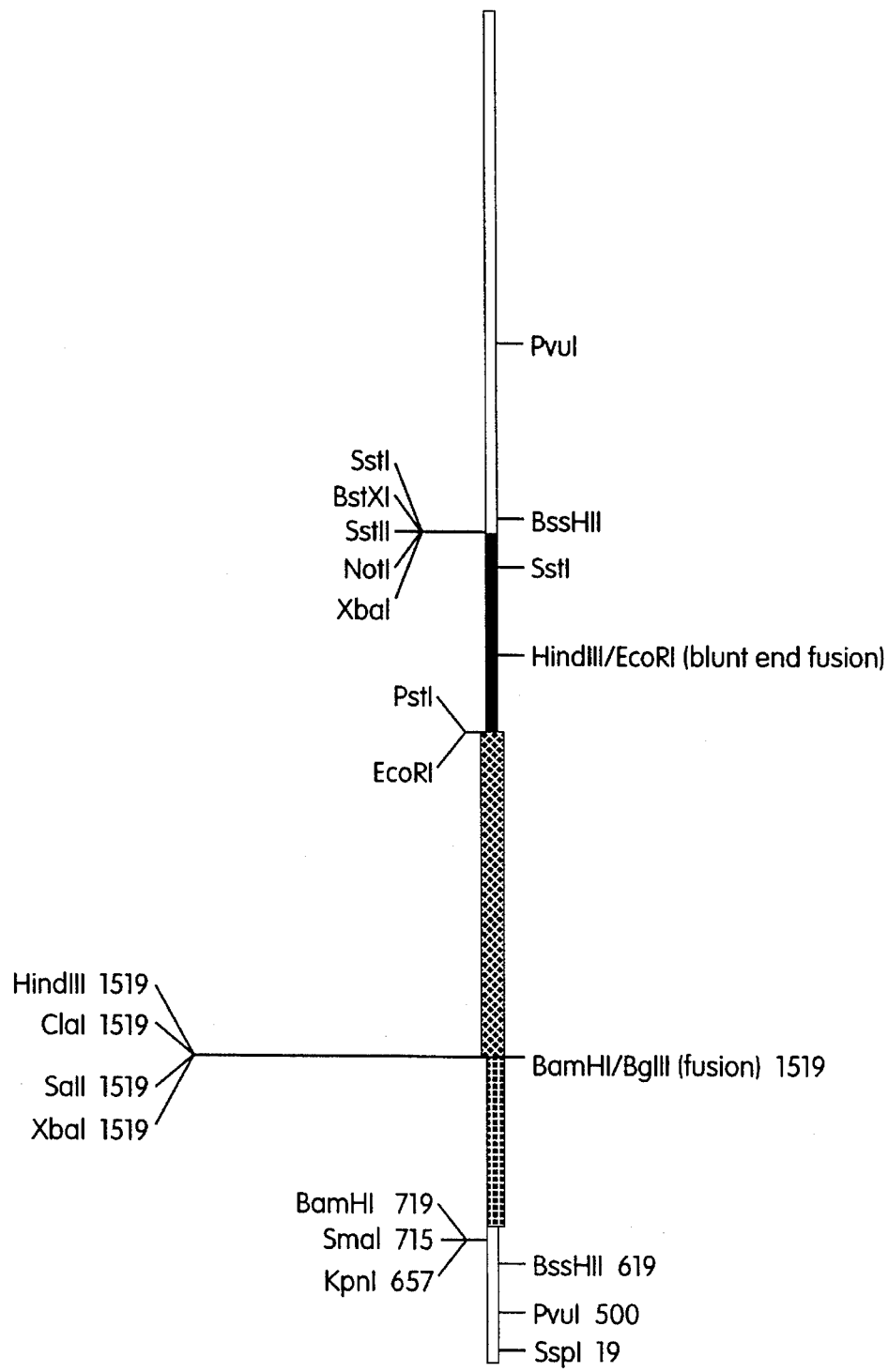

FIG. 8 is a schematic map of an expression system in accordance with the present invention, TAP MYOD. In the Figure, the open bar represents the sequence from Bluescript II+; the hatched bar is from SV40 and contains the small t splice and polyadenylation signals; the closed bar is from aP2 promoter and the circle bar comprises the DNA sequence coding for the muscle transcription factor, MYOD. Coordinates are approximate.

Figure 9:
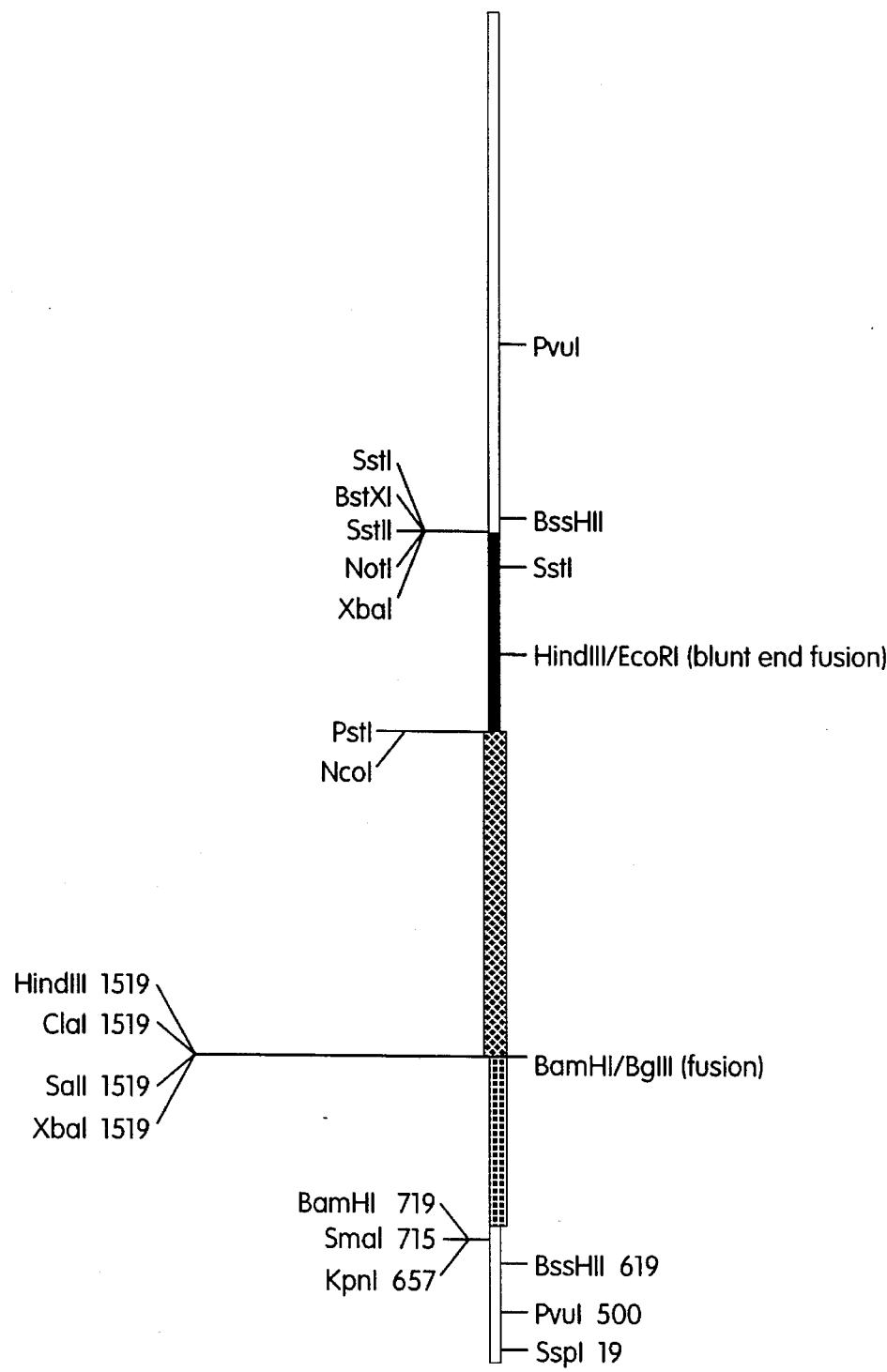

FIG. 9 is a schematic map of an expression system in accordance with the present invention, TAP $\alpha_2$ adrenergic. In the Figure, the open bar represents sequence from Bluescript II+; the hatched bar is from SV40 and contains the small t splice and polyadenylation signals; the closed bar is from aP2 promoter and the circle bar comprises the DNA sequence coding for the α2 adrenergic receptor. Coordinates are approximate.

Figure 10:
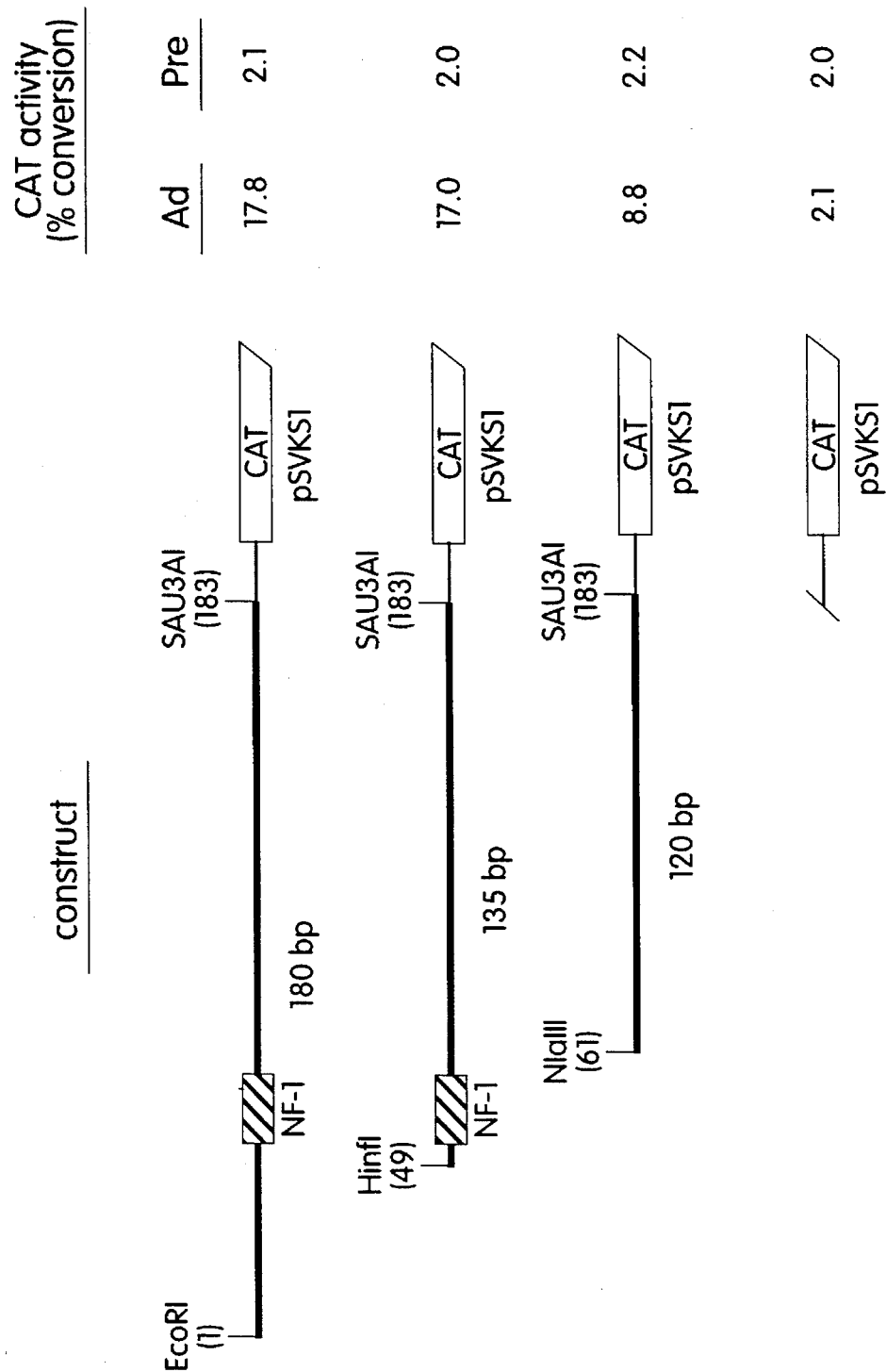

FIG. 10 is a schematic map of deletion constructs of the EcoRI-Sau3AI restriction fragment of the 518 base pair aP2 enhancer tested for their ability to stimulate CAT gene expression from the enhancerless SV40 vector in reporter vector pSVKSI when transiently transfected into cultured preadipocytes (Pre) or adipocytes (Ad). The size of the restriction fragments, indicated by the heavy bar, is also indicated with the base pair coordinates in relation to the whole enhancer. The NFI-site is indicated by the stippled box. CAT activity from the transient transfections is indicated.

Figure 11:
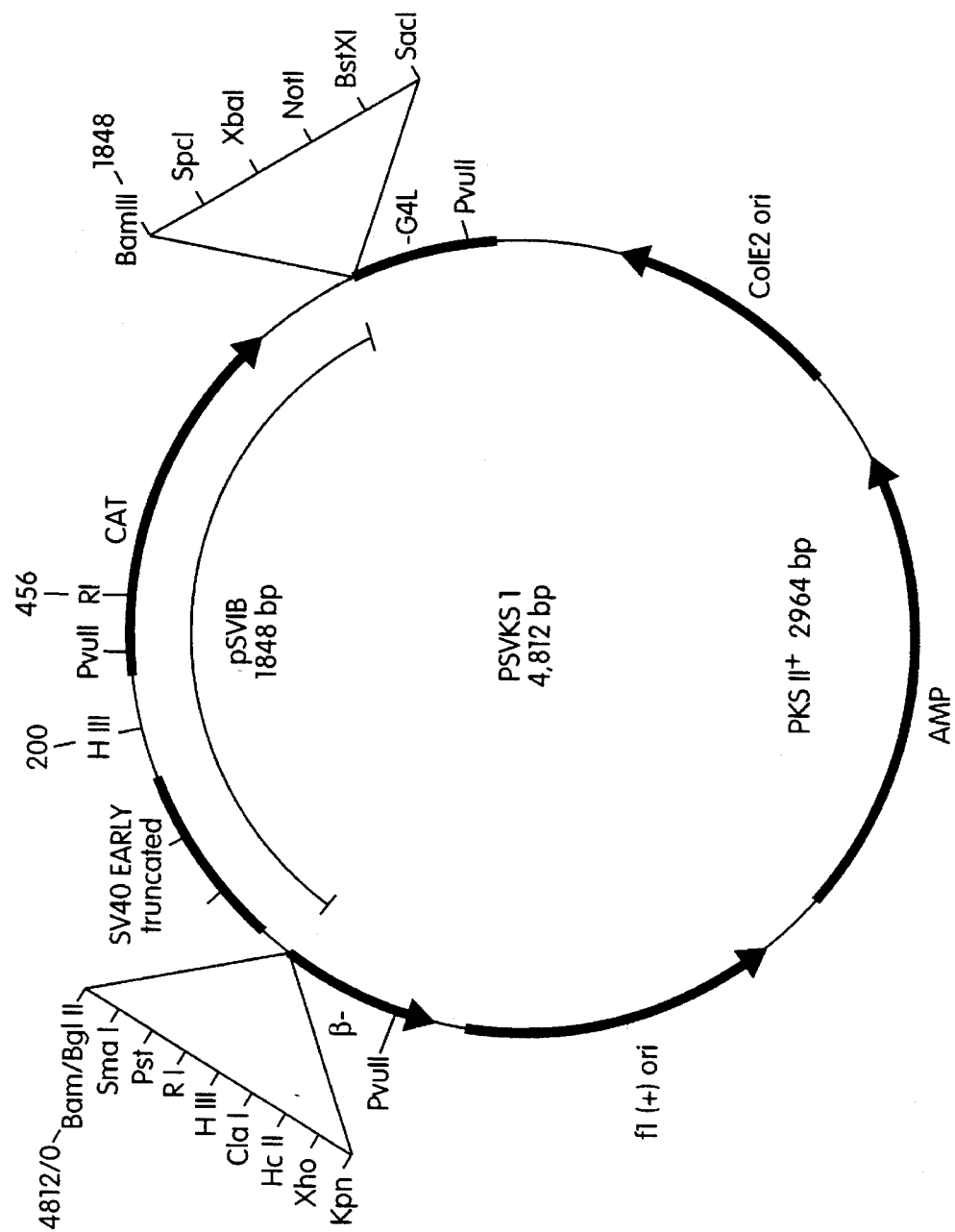

FIG. 11 is a schematic map of the reporter vector pSVKSI used in the experiments described in Example 5.

FIG. 12 depicts the important regions of the competitive oligonucleotides used in mobility shift assays to assess the binding of nuclear proteins to a double-stranded oligonucleotide spanning the ARE2 region, comprising nucleotides 114 to 146 of the AP2 enhancer of SEQ. ID. No. 1. In FIG. 12, the depicted ARE2 nucleotides correspond to SEQ. ID. No. 5, while the depicted ARE4 nucleotides correspond to SEQ. IN. NO. 6. Changes in the DNA sequence that result in mutations of the protein binding site are indicated by the underlining in ARE2 M1, an ARE2-containing mutant that corresponds to SEQ. ID. NO. 7.

Figure 13:
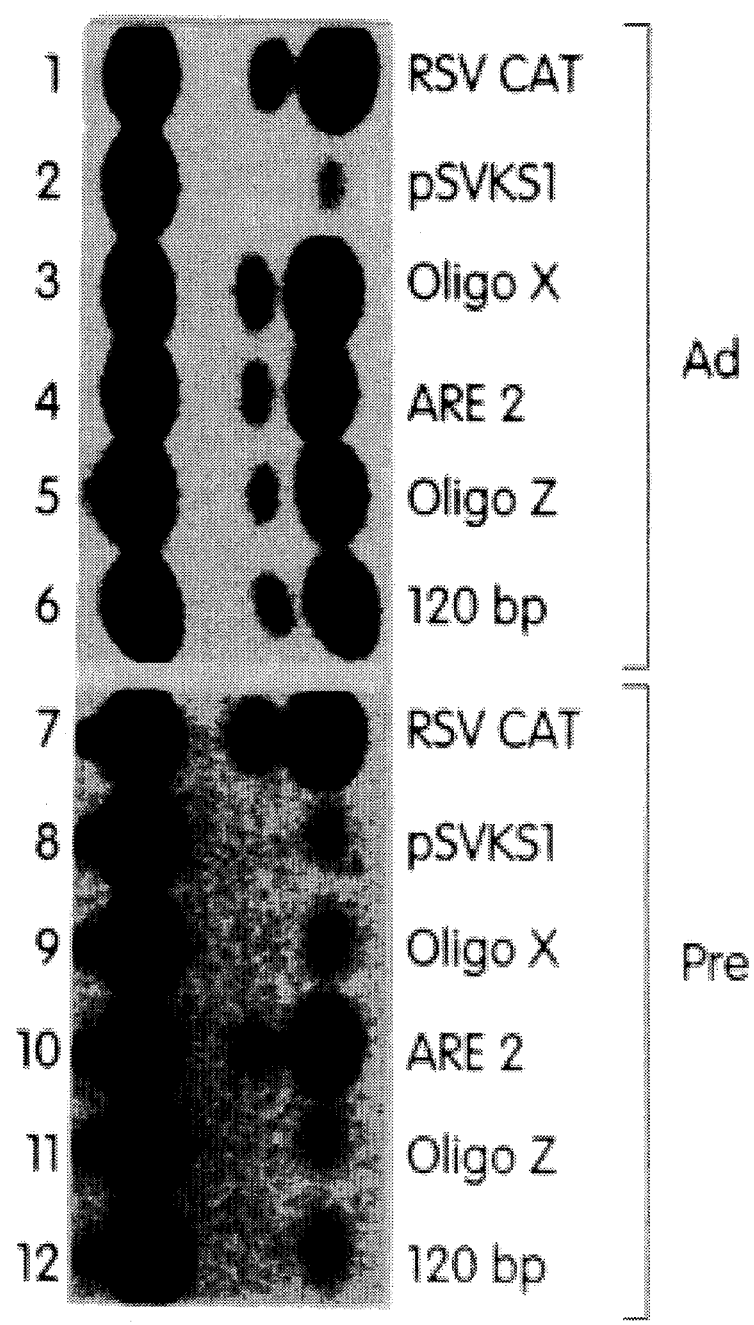

FIG. 13 is an autoradiograph depicting the results of CAT assays from adipocytes (Ad, lanes 1–6) or preadipocytes (Pre, lanes 7–12) transiently transfected with pSVKSICAT (lanes 2 and 8) or pSVKSICAT constructs containing: lanes 3 and 9, three copies of oligonucleotide X in an inverted orientation relative to its orientation in the endogenous gene; lanes 4 and 10, three copies of the ARE2 oligonucleotide; lanes 5 and 11, three copies of oligonucleotide Z in tandem in an inverted orientation and lanes 6 and 12, the 120 bp NlaIII-Sau3AI restriction fragment. All inserts were in the SmaI site of the vector. The RSVCAT vector was also transfected, lanes 1 and 7. Oligonucleotide X is base pairs 61 to 116 of the 518 base pair murine aP2 enhancer element; oligonucleotide Z is base pairs 138 to 181 of the 518 base pair enhancer element.

Figures 14A, 14B:
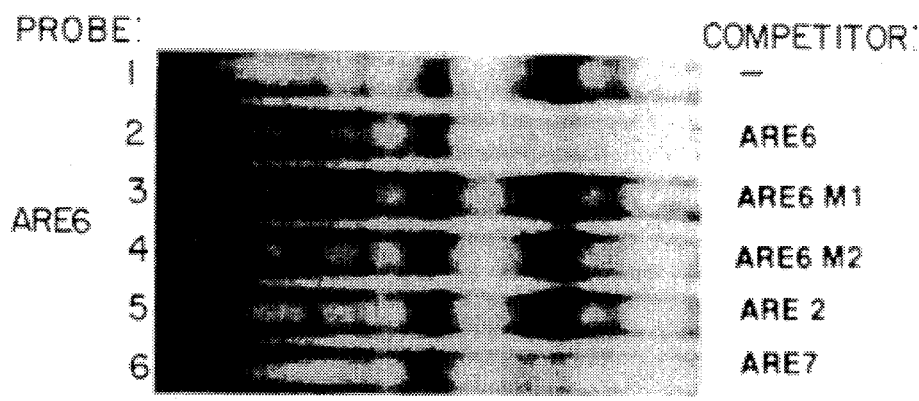
Figure 14C:
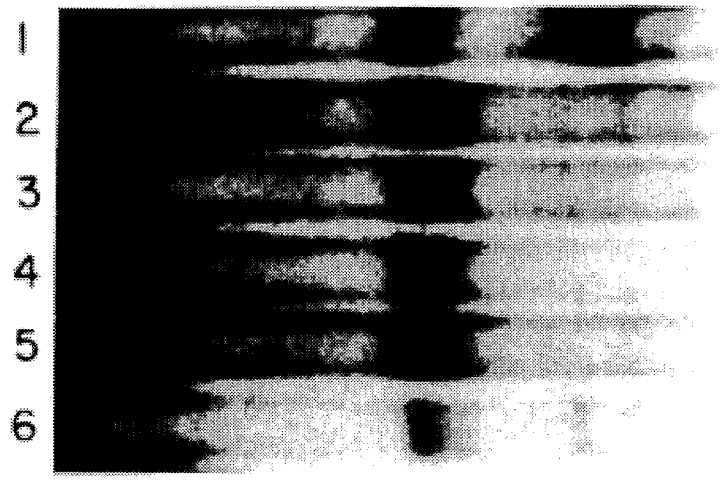

FIG. 14 comprising FIGS. 14A–14C depicts the sequence and protein-binding assays of ARE6-containing oligonucleotides.

FIG. 14A provides a sequence comparison of the ARE6 and ARE7 motifs (shaded) and flanking regions from the aP2 enhancer. In FIG. 14A, the ARE-6 motif-containing nucleotide sequence corresponds to the nucleotide sequence set forth in SEQ. IN. NO. 8, while the ARE-7 motif-containing nucleotide sequence corresponds to the nucleotide sequence set forth in SEQ. ID. NO. 9. The sequences identified in FIG. 14A as ARE6 M1 and ARE6 M2 represent two nucleotide sequences containing a mutation in the ARE 6 site, which oliogonucleotides were unable to compete for binding to double-stranded oligonucleotide containing an ARE 6 binding site. The oligonucleotides correspond to SEQ ID NOS 10 and 11, respectively.

FIG. 14B is an autoradiograph showing the sequence specificity of ARE6. Double-stranded oligonucleotides containing an ARE6-binding site were radiolabeled and then incubated with nuclear extracts from adipocytes. DNA-protein complexes were resolved from free DNA by electrophoresis on polyacrylamide gels. Sequence specificity of protein binding was assessed by inclusion of a 50 molar excess of various double stranded oligonucleotides, as described in Example 5 and indicated at the top of the wells. A minus sign indicates that no competitor was added.

FIG. 14C is an autoradiograph demonstrating that the double-stranded ARE6-containing oligonucleotide binds a protein factor found in adipocyte nuclear extract (3T3F44a), but not in the nuclear extract of preadipocytes (3T3F44a preadipocyte preparations 1 and 2) or in other cultured cell lines 3T3C2, C2C12 or HeLa.

DEFINITIONS

As used in this application and claims, the terms recombinant protein and operatively linked have the following definitions:

Operatively linked—the linking of an adipose-specific DNA sequence to a DNA sequence coding for a desired protein so as to permit expression of that DNA sequence and production of that protein.

Recombinant protein—a protein or peptide coded for by a DNA sequence which is not endogenous to the native genome of the animal in whose adipose tissue it is produced in accordance with this invention or a protein or peptide coded for by a DNA sequence which, if endogenous to the native genome of the animal in whose adipose tissue it is produced, does not lead to the production of that protein or peptide in adipose tissue at the same level that the transgenic animal of this invention produces in adipose tissue.

DETAILED DESCRIPTION OF THE INVENTION

This invention relates to processes, DNA sequences, compositions of matter and transgenic animals. In one embodiment, the invention relates to the transgenic incorporation of one or more copies of an expression system or construct comprising an adipose-specific DNA sequence operatively linked to a DNA sequence coding for a recombinant protein capable of exerting an effect on adipose tissue metabolism. The construct is introduced transgenically into the germ line of an animal or ancestor thereof at an embryonic stage and the recombinant protein is expressed primarily in the adipose tissue of the animal. Depending upon the nature of the recombinant protein coded for by the DNA sequence, the transgenic animals are either leaner or more obese than nontransgenic controls.

In another embodiment, the invention relates to shorter DNA sequences within the adipose-specific DNA sequences that are primarily responsible for adipose-specific expression of the gene. These sequences bind a trans-acting adipose regulatory factor (ARF) present in the nuclear extract of differentiated adipocytes, but not preadipocytes, and activate gene activity specifically in differentiated adipose cells.

Adipose-Specific Control Sequences That Regulate In Vivo Gene Expression

The regulatory DNA sequences of the present invention, sometimes hereinafter referred to as adipose-specific DNA sequences, are primarily located in the 5' flanking region of genes expressed primarily in differentiated adipocytes. The DNA sequences can be enhancer sequences which, when operatively linked to a gene through a functional promoter, are capable of directing adipose-specific expression of the gene in the animal. Alternatively, the adipose-specific DNA sequences may be located within the promoter region.

In accordance with one embodiment of the present invention there is provided a functional, adipose-specific control sequence isolated from the murine adipocyte P2 (aP2) gene. The aP2 upstream control element is an enhancer sequence, comprising about 518 nucleotides [SEQ ID NO. 1], and is contained in the 5' region of the murine aP2 gene, at about nucleotides −5.4 kb to −4.9 kb (an EcoRI-XbaI restriction fragment). When linked to a DNA coding sequence through a functional promoter, this ≈518 base pair sequence is capable of directing the adipose-specific expression of the gene in vivo. Larger regions of the 5' flanking regions can similarly be used, as long as the 518 bp are included in the sequence.

It will be appreciated by those skilled in the art that variations in the functional enhancer sequence may exist due to genetic polymorphisms or cell-mediated modification of the genetic material. Furthermore, the DNA enhancer sequence can be manipulated by genetic techniques to produce a slightly different sequence of bases. Such sequences are within the scope of the present invention where the ability of the sequence to direct fat-specific expression in the animal is retained. For example, smaller fragments or deletions of the 518 base pair sequence may be useful in directing fat-specific expression in vivo. A method for preparing and screening smaller fragments is described in the examples herein. Methods of preparing deletion mutations are conventional in the art; such mutants can similarly be screened as discussed herein.

Also provided is an adipose-specific DNA sequence isolated from the 5' region of the murine adipsin gene. The adipsin adipose-specific sequence [SEQ ID NO. 2] is located at about nucleotides −114 to +35 of the murine adipsin gene, a region which also includes the promoter for the gene. When linked to a gene in the proper orientation, this 149 base pair sequence is also capable of directing fat specific expression of genetic material in vivo. For promoter sequences such as the murine adipsin sequence, a heterologous enhancer can be employed to increase the level of adipose-specific expression. Examples of suitable enhancer sequences include, but are not limited to, the Akv viral enhancer, the SV40 viral enhancer, the murine sarcoma virus enhancer and the aP2 enhancer element.

Additional adipose-specific DNA sequences can be isolated from other adipose differentiation-linked genes using the methodology described herein, which will similarly be useful in the generation of the transgenic animals with altered fat metabolism. Examples of other adipose differentiation linked genes include, without limitation, the genes encoding glycerophosphate dehydrogenase (GPD), and stearoyl CoA reductase, hormone sensitive lipase and lipoprotein lipase.

Suitable Promoters

The expression systems or constructs of the present invention comprise an adipose specific DNA sequence operatively linked to a DNA sequence coding for a recombinant protein capable of exerting an effect on the metabolism of adipose tissue. Where the adipose-specific sequence is an enhancer sequence, the operative linkage is through a functional promoter.

Promoter DNA sequences suitable for use with the enhancer sequences of the present invention include both homologous and heterologous promoters. For sequences comprising the 518 base pair murine aP2 enhancer sequence, a suitable homologous promoter is a basal promoter comprising nucleotides −63 to +21 of the murine aP2 gene (nucleotides 52–134 of SEQ ID NO.2)

The enhancer sequences of the present invention can also be linked to the DNA coding sequence through a heterologous promoter. Suitable heterologous promoters may include promoters which are functionally responsive to environmental variations in the concentrations of metals and/or steroid hormone compounds. These inducible promoters include promoter sequences which are naturally associated with the transferrin gene of chickens, the steroid/hormone responsive gene associated with the ovalbumin gene of chickens and the metal and steroid hormone responsive promoter of the mouse metallothionein genes. Sequences which are neither hormone nor metal responsive which can be used in accordance with the present invention include the truncated SV40 promoter, liver promoters, immunoglobulin gene promoters and heat shock promoters.

Of the heterologous promoters, the truncated SV40 or metallothionein promoter is preferably employed.

DNA Coding Sequences

The DNA coding sequences to be expressed fat-specifically in transgenic animals in accordance with the present invention are DNA sequences which code for a recombinant protein capable of exerting an effect on the growth and/or metabolism of fat cells. The DNA coding sequences can either be endogenous or exogenous to the animal whose metabolism is to be altered and the effect of the genes can be either direct or indirect. Genomic or cDNA can be used.

The DNA coding sequences to be expressed in adipose tissue of the transgenic animals include sequences coding for recombinant proteins which exhibit a lipolytic effect on adipose cells. Such proteinaceous materials are characterized by an ability to decompose or break fat down. The expression of proteins or polypeptides in adipose tissue that have a lipolytic effect on fat tissue will have a leaning effect on transgenic animals bearing the transgene. Similarly, proteins having an anti-lipogenic effect can result in leaner animals.

The DNA sequence can alternatively code for proteins that have a lipogenic effect on adipose cells, characterized by an ability to cause fat formation. Expression of proteinaceous materials in fat tissue which exert a lipogenic effect will result in increase fat formation, resulting in animals which are obese. Anti-lipolytic factors, which cause a decrease in fat decomposition, would also be expected to result in more obese animals.

Numerous factors which have an effect on adipose tissue metabolism are known. These factors can broadly be categorized into several different classes of proteinaceous materials, including hormone receptors, oncogenes, ligands, enzymes and transcription factors. Examples of each of these classes and materials are provided below.

Hormone Receptors

Genes encoding hormone receptors that can be used in accordance with the present invention include those encoding the alpha and beta adrenergic receptors, the growth hormone receptor and wild type and mutant insulin receptors. The beta adrenergic receptors, including $\beta_1$, $\beta_2$ and $\beta_3$, are transducers of catecholamine action in fat cells and have a lipolytic effect on these cells. Gilman et al., "The pharmacological basis of therapeutics", MacMillan Publishing Co., New York, Chapter 8:145–180 (1985). An overexpression of this receptor in fat tissue will have a leaning effect in animals bearing this transgene.

The $\alpha_2$ adrenergic receptor, which also binds catecholamines, has an anti-lipolytic effect on adipose cells (Berlan et al., Eur. J. of Clin. Invest., 15:341–348 (1985); Galitzky et al., Eur. J. of Clin. Invest., 18:587–594 (1988)) and its overexpression in fat cells will cause a decrease in the rate of triglyceride breakdown. This will result in a decrease in fat breakdown and the animal will be obese.

The growth hormone, acting through its specific receptor, causes fat breakdown. Expression of the gene encoding the growth hormone receptor causes increased lipolysis in adipose tissue, which will have a leaning effect in the animals bearing this transgene.

The insulin receptor is responsible for the lipogenic, anti-lipolytic effects of insulin. The wild type insulin receptor increases lipid accumulation when overexpressed in fat. Overexpression of the wild type insulin receptor in fat will lead to an increased fat accumulation resulting in an obese animal. Alternatively, there are known mutations in the insulin receptor that inactivate its function and also inactivate other wild-type receptor molecules present in the same cells. Overexpression of these "dominant-negative" insulin receptors will result in a decreased sensitivity of fat cells to insulin, resulting in animals that have a decreased level of fat storage. Such animals will be lean.

oncogenes

Various oncogenes or protooncogenes can interfere with fat cell differentiation and fat storage in cultured adipocytes. Examples of such oncogenes include c-myc (Freytag, S. O., Mol. Cell Biol., 8:1614–1624 (1988)) and the SV40 large T antigen (Cherington et al., Mol. Cell Biol., 8:1380–84 (1988) or c-ski (Sutrave et al., "Genes and Development", in press (1990)). These genes can be linked to the upstream adipose-specific control sequences of the present invention and interfere with the ability of fat cells to differentiate or carry out their lipid accumulation pathways. Overexpression of these gene products may or may not result in tumor formation.

Ligands

There are a large number of polypeptides that influence adipose tissue to store or breakdown triglycerides. The genes for these ligands include, but are not limited to: insulin (lipogenic); growth hormone (lipolytic); tumor necrosis factor (lipolytic); glucagon (lipolytic); and adrenal corticotropic hormone (lipolytic). Expression of these secreted peptides from adipose cells should cause a higher level of expression present in adipose tissue than in the systemic circulation, resulting in greater effects in adipose tissue than in other tissues.

Enzymes

In accordance with the present invention, it is also possible to directly overexpress several intracellular enzymes or extracellular enzymes that are involved in pathways of accumulation or breakdown of triglycerides in adipose cells, Examples of such enzymes include without limitation: hormone sensitive lipase (lipolytic); stimulatory G protein (lipolytic); inhibitory G protein (lipogenic); fatty acid synthetase (lipogenic); lipoprotein lipase (lipogenic) and acetyl CoA carboxylase (lipogenic).

Transcription Factors

It is also possible to interfere with adipose tissue development by expression in fat cells of a transcription factor specific for another developmental lineage, such as muscle. By expression of MYOD1, a muscle transcription factor, it is possible to interfere with fat development and alter this development to the muscle lineage. An animal bearing this transgene will be leaner and should also be more muscular than non-transgenic animals of the same species.

Other proteinaceous materials capable of exerting an effect on the metabolism of fat cells will be apparent to those skilled in the art and are considered within the spirit and scope of the present invention.

Expression Systems

The constructs or expression systems of the present invention are prepared by operatively linking the DNA coding sequence to the adipose-specific DNA sequence. For enhancer sequences, such as the murine aP2 enhancer, the operative linkage of the enhancer to the structural gene is through a functional promoter. Generally, the adipose-specific upstream enhancer sequence is placed upstream of the promoter sequence, and can be linked in either a 5' to 3' or inverted (3' to 5') orientation. Alternatively, where the adipose-specific DNA sequence is itself located within a promoter region, the adipose-specific sequence is operatively linked directly to the functional gene in a '5 to 3' orientation.

Preferably, the expression system or construct of this invention also includes a 3' untranslated region downstream of the DNA sequence coding for the recombinant protein. Among the 3' regions which are preferably employed are sequences that provide mRNA splice and polyadenylation signals. Such sequences may be derived, for example, from the SV40 small t antigen or other 3' untranslated sequences well known in the art.

Methods for producing the above-described expression systems are well known. For example, various ligation techniques employing conventional linkers, restriction sites, etc., may be used to good effect. Preferably, the expression systems are prepared as part of larger plasmids. Such preparation allows the cloning and selection of the correct constructions in an efficient manner, as is well known in the art. Most preferably, the expression systems are located between convenient restriction sites on the plasmid so that they can be easily isolated from the bulk plasmid sequences.

Transgenic Animals

The transgenic animals of the present invention are obtained by introducing the linearized construct or expression system into the animals at an embryonic stage. The animals which can be usefully employed in accordance with the present invention are not particularly limited, and can include laboratory animals such as mice, rats, guinea pigs, rabbits, monkeys and domestic livestock, including cattle, pigs, sheep and chickens. The adipose-specific DNA sequence employed in the expression system need not be endogenous to the animal whose germ line is to be altered. Thus, for example, the murine aP2 enhancer sequence can be utilized to direct the adipose-specific expression of a transgene in other animals, such as pigs. For practical reasons, it may be preferable to use a control sequence endogenous to the animal whose germ line is to be altered. In view of the known sequence homology of adipose differentiation-linked genes, such adipose-specific sequences can readily be obtained using the murine sequences described herein as hybridization probes.

In addition, a particular adipocyte-specific sequence may be more effective in one animal than others. One of skill in the art can readily make such choices by following the teachings of the invention.

Techniques for introducing transgenes into genetic material are known and have become conventional in the art. The following references, which describe procedures that can be used in accordance with the present invention, are hereby incorporated by reference. Evans et al., U.S. Pat. No. 4,870,009, Miller et al., *Journal of Endocrinology*, 120:481–488 (1989); Hammer et al., *J. Anim, Sci.*, 63:269–278 (1986) and Hammer et al., Cold Spring Harbor Symposium, Quant. Biol., 50:379–387 (1985).

Briefly, a fertilized egg is obtained from the animal and the constructs are introduced into the fertilized egg in linear form. Several methods have successfully been employed to introduce foreign DNA into the genetic material of mice, including microinjection of eggs, retrovirus infection of embryos, embryonic transfer of stem cells in blastocysts (Pursel et al., *Science*, 244:1281 (1989), and spermatozoa-mediated transfer of DNA (Lavitrano, *Cell*, 57:717–723 (1989). For domestic animals, such as livestock, microinjection of the constructs into embryos is the method of choice. Preferably, the DNA is injected into the pronucleus of one cell eggs or the nucleus of two cell eggs.

Visualization of the nuclei of some animals, such as rabbits and sheep, can be aided through the use of interference-contrast (IC) microscopy. For less visible nuclei, such as those obtained from pigs and chickens, interference contrast microscopy alone will generally be insufficient. In such instances, visibility for microinjection can be enhanced by first centrifuging the eggs, followed by I-C microscopy. Wall et al., *Biol. Rep.*, 32:645 (1985).

The fertilized eggs having the fusion gene are then implanted into a host female of the species from which the fertilized eggs were obtained, so that the host female gives birth to a transgenic animal that develops from the fertilized egg. Usually, about 20–40% of the animals developing from the injected eggs contain at least one copy of the cloned fusion gene in somatic tissues and the transgenic animals usually transmit the gene through the germ line to the next generation. For those species which give birth to more than one offspring, non-transgenic siblings provide an excellent control for determination of altered fat metabolism and fat tissue content.

The living transgenic animals and their progeny producing the metabolism-altering proteinaceous materials (which for purposes of this invention are considered the equivalent of the first generation transgenic animal) are continuous sources of leaner or more obese animals.

Offspring are tested for the presence of the transgene using techniques well known to those skilled in the art. For example, total nucleic acid can be extracted from a piece of the tail of the offspring and used for DNA dot hybridization according to the technique of Southern (*J. Mol. Biol.*, 98:503 (1975)) to determine which animals carry the transgene. Labeled DNA or RNA probes complementary to a portion of the gene are employed in the hybridization and animals that yield hybridization signals above the background are detected. Alternatively, polymerase chain reaction using appropriate probes can be employed to detect the presence of the transgene in the sample of total nucleic acid.

Altered fat metabolism in the transgenic animals resulting from the expression of the transgene in adipose tissue can be detected in a number of different ways. In rodents, such as mice, altered fat metabolism can be detected by measuring adipose cell volume and also by measuring fat pads. The latter technique involves sacrificing the animals and then removing and weighing the fat pads (gonadal, peri-adrenal, subcutaneous and abdominal). Other analyses, including determination of rates of fatty acid synthesis and/or lipolysis, determination of blood-lipid composition, in vivo, assays of $^{14}$C-labeled glucose incorporation into adipose tissue and adrenergic agonist and antagonist treatments of the animals, may also be employed.

In livestock, such as pigs and sheep, altered fat tissue metabolism can be detected by measuring back fat content in accordance with various techniques known in the art. For example, metabolism in the rump region has previously been shown to be representative of back fat. Subcutaneous back fat content can therefore be determined taking biochemical measurements from transgenic and control animals of the same species. In accordance with this method, tissue can be removed surgically from the rump region of the offspring and subjected to enzyme assays as previously described. The rate of fatty acid synthesis in adipose tissue samples can be determined as described by Sinnett-Smith and Woolens, *Anim. prod*, 45:75–80 (1987). Rates of lipolysis can determined by measuring the rates of glycerol release from adipose tissue. Sinnett-Smith and Wollens, *Anim. prod.*, 47:263–270 (1988). See also, Sinnett-Smith and Woolens, *Int. J. Biochem.*, 21:535–540 (1989).

Other techniques for assessing altered adipose tissue metabolism include ultrasonic and direct back fat measurement. Magnetic resonance imaging can also be employed. Real time ultrasound is particularly preferred, as it causes less stress to the animals than other techniques which require surgical intervention and has become a reliable technique for determining fat content, particularly in the pork industry. Terry et al., *J. Anim. Sci.*, 67:1279–1284 (1989); Mersmann, *J. Anim. Sci.*, 54:268 (1982).

Adipose Regulatory Elements That Bind A Trans-Acting Factor In Adipocyte Nuclear Extract The regulation of genes is often elaborated through the interaction of several transcription factors, usually proteins, that have binding sites clustered within enhancer sequences. In accordance with the present invention, we have identified several different regulatory sequences located generally within the most 5' end of the aP2 enhancer herein described that bind trans-acting adipose regulatory factors (ARF's) or proteins. In each instance, the binding of the factor to its recognition sequence appears to be critical to full enhancer activity and transcription of the gene. However, one sequence of about 10–12 base pairs within the murine aP2 enhancer sequence, identified herein as adipose regulatory ARE6 binds to a nuclear protein(s) found in differentiated adipocyte, but not preadipocyte, nuclear extracts. The binding of this nuclear factor to its cognate sequence appears to be the key to the differentiation dependent activity of the aP2 enhancer element.

In another embodiment of this invention, regions of DNA containing the sequences critical to differentiation-dependent adipose gene expression and the nuclear protein(s) that bind to them can be utilized in screening for pharmacoactive organic molecules that inhibit the DNA-protein binding. Molecules that inhibit the binding of the protein factor to ARE6-containing sequences are in turn excellent candidates for therapeutic intervention in adipose tissue disorders, and particularly obesity.

Obesity is a heterogeneous disorder characterized by an excessive mass of adipose tissue. This disease arises through an increased number of adipocytes or an excessive lipid accumulation in the cell or both. Without wishing to be held to any particular theory or mechanism of the invention, the inventors herein believe that prevention of the binding of the ARE6-specific factor(s) to its cognate sequence will block differentiation, resulting in fewer adipose cells.

A number of screening assays useful in the identification of pharmacoactive molecules that interfere with the binding of the nuclear factor to their target sequences will readily be appreciated by persons skilled in the art based upon the teachings herein. One example of a screening assay involves the tandem multimerization of an appropriate oligonucleotide and insertion of the multimerized sequence into a vector including an indicator gene, for example, chloramphenicol acetyltransferase ("CAT"). The resulting vectors are transiently transfected into differentiated adipocytes using conventional techniques and incubated for an appropriate period of time.

The test molecules are also added to the cultures and the cells subjected to further incubation. After a sufficient period of time, cell extracts are prepared and the activity of the indicator gene measured. Small molecules that exert an inhibitory effect on the binding of the adipose nuclear factor which binds ARE6-containing sequences will exhibit a concentration dependent inhibition of gene expression. Such molecules should then be cross-assayed against various other elements, in order to identify molecules that show specificity for the ARE6-protein binding and do not inhibit other important DNA-protein binding activities.

A second assay, which provides for a more rapid screening of molecules, involves the use of DNA-protein binding mobility shift assays. In accordance with this technique, nuclear extracts or purified binding proteins obtained from differentiated adipocytes are incubated with a labeled DNA sequence including one copy of ARE6-containing sequences, either alone or simultaneously with varying concentrations of organic test molecules. After incubation, samples are loaded on a polyacrylamide gel and electrophoresed in a suitable buffer. Gels are then dried, exposed to X-ray film in accordance with standard protocols, and reviewed in order to identify small molecules that interfere with DNA-protein binding.

Nuclear extracts from adipocytes can be obtained in accordance established protocols, as described, for example, in Shapiro et al., *DNA*, 7(1):47–55 (1988) and Dignam et al., *Nucl. Acids Res.*, 11:1475–1489 (1983). As an alternative to nuclear extracts, the adipose regulatory factor can either be molecularly cloned or purified from nuclear extracts and utilized in the DNA mobility shift assays to screen for inhibitory molecules. The adipose regulatory factor can be cloned using expression cloning techniques in the bacteriophage lambda, as described in Sambrook, Fritsch and Maniatis, *Molecular Cloning*, §§ 12.30–12.40, using double stranded multimerized (concatenated) ARE6-containing sequences as probes in the screening of expression libraries. Purification of the protein factor from adipocyte nuclear extracts can be accomplished using gel filtration and sequence-specific affinity chromatography techniques, using ARE6-containing nucleotide sequences, as previously described. See, e.g., Jones, *Cell*, 48:79–89 (1987). The proteins can then be subjected to amino acid analysis using any of the known techniques.

The foregoing assays are provided for illustrative purposes and are not meant to be a limitation on the methods that can be used to screen for molecules that interfere with DNA-protein binding interactions. Variations of these assays will be readily appreciated by persons skilled in the art.

Organic molecules that can be tested in the assays of the invention include oligonucleotides based upon the ARE6 sequence, as well as a random library of orally active organic molecules and peptides and proteins derived from the ARE6-specific factor. Particularly promising candidates for effecting inhibition are nucleotides based upon the actual DNA binding sites for the ARE6-specific nuclear factor.

Molecules that specifically inhibit binding of the ARE6-specific factor to its cognate sequence can be used to screen for anti-obesity effects in animals. Many different animal models are available for obesity research, as described by Douglas Coleman in "The Mouse in Biomedical Research, *Experimental Biology and oncology*, Foster et al., ed., Academic Press (1982). Particularly preferred are mice having an ob autosomal recessive mutation (chromosome 6) (the "ob/ob mouse"), established in the C57BL/6J strain, the db/db diabetes mouse (autosomal recessive mutation, chromosome 4; available from Jackson laboratories) and the Zucker rat (autosomal recessive, fa/fa).

For conduct of animal studies, adult obese animals, such as Zucker rats, and weight matched lean littermates (Fa/Fa or Fa/fa) are housed in temperature regulated, light/dark cycled rooms in cages. Animals can have free access to food and water and should be allowed to acclimatize to their environment prior to the start of any experimentation. Small molecules are formulated in a suitable dosage form and administered via a suitable drug delivery system, selected from, for example, subcutaneous or intramuscular injection administered via conventional syringes, external infusion pumps and injection pens, as well as via transdermal., buccal., nasal and oral absorption. Depending upon the nature of the therapeutic molecule, the delivery system may require the inclusion of absorption enhancers or carriers, such as surfactants, mucolytic reagents and/or enzyme inhibitors.

The effect of the small molecule or drug is determined by comparing the results obtained with the treated animals with those obtained for paired fed, weight matched, control obese animals that have been injected with a drug vehicle during the treatment period. Decreased adipose content can be determined by weighing the live animals or by sacrificing the animals and weighing fat pads. Other methods of determining fat content described above can alternatively be employed.

Utility

The adipose-specific DNA sequences of the present invention are useful in the generation of transgenic animals exhibiting altered fat tissue metabolism. In addition, the adipocyte specific enhancers and the ARE sequences embedded therein can be used for the development of drugs to alter fat cell function and treat obesity.

The transgenic animals of the present invention, exhibiting altered levels of endogenous gene products, can be used as models to obtain a more complete understanding of the role of such genes in adipose tissue, both in adipose homeostasis and in the disease states involving this tissue. For example, it is known the adipsin is deficient in several animal models of obesity. Flier et al., *Science*, 237: 402– 405 (1987); Platt et al., *Proc. Natl. Acad. Sci.*, 86: 7490– 7494 (October 1989); Wilkison et al., *J. Biol. Chem.*, 265: 477–482 (January 1990). To gain a better understanding of adipsin's physiological role in obesity, the adipsin gene can be overexpressed in adipose tissue of obese mice in accordance with the present invention. The mice will have adipsin sequences (cDNA and/or genomic) under the control of the aP2 enhancer, which is not regulated by the obese state of the animal. The aP2 adipsin transgenic animals will show increased levels of adipsin expression in adipose tissue due to expression of the transgene.

The transgenic animals of the invention can also be used to test the efficacy of pharmaceutical agents designed to control disorders associated with adipose tissue.

When the invention is applied to commercially important livestock, the animals can be used as continuous sources of feed animals which exhibit reduced fat content.

Deposits

A first construct according to this invention, prepared in accordance with Example 7 herein is exemplified by a culture deposited in the American Type Culture Collection, Rockville, Md., on Sep. 25, 1990, and there identified as pTAP-MYOD. It has been assigned ATCC accession No. 40895.

A second construct according to this invention, prepared in accordance with Example 8 herein is exemplified by a culture deposited in the American Type Culture Collection, Rockville, Md., on Sep. 25, 1990, and there identified as pTAP-α2. It has been assigned ATCC accession No. 40894.

The present invention will be more readily understood from the following specific examples.

EXAMPLE 1

This example demonstrates that a murine aP2 DNA enhancer sequence conferring adipose-specificity in vivo is located between −5.4 and −1.7 kb, in the 5' flanking region of the murine aP2 gene. This example also demonstrates that the aP2 promoter region previously shown to function in a differentiation dependent manner in adipocytes in culture (−168 to +21, Distel et al., *Cell*, 49:835–844 (Jun. 19, 1987)) is insufficient to drive expression in vivo.

Preparation of Constructs

The aP2 sequences used in the preparation of the constructs were isolated from aP2 genomic DNA from lambda phage clone aP2911, available from Dr. Bruce Spiegelman of the Dana-Farber Cancer Institute, Boston, Mass. A restriction map of the murine aP2 5' flanking region used to construct the transgenes is illustrated in FIG. 1B. See also, Hunt et al., *Proc. Natl. Acad. Sci.*, 83:3786–3790 (1986).

Four constructs, containing either 168 base pairs (bp), 247 bp, 1.7 kilobases (kb) or 5.4 kb of the aP2 5' flanking region of the murine adipocyte P2 gene linked to chloramphenicol acetyltransferase gene sequences and the SV40 small t antigen splice site and polyadenylation signals, were obtained. Chloramphenicol acetyltransferase (CAT) is a bacterial gene encoding an enzyme which is widely used in the study of gene regulation. The expression of this enzyme in mammalian cells provides a sensitive, albeit indirect, assay for the transcriptional activity of particular DNA fragments in transient transfections.

The vectors used for the 168aP2CAT and 247aP2CAT transgenes have previously been described. See, Distel et al., *Cell*, 49:835–844 (Jun. 19, 1987). Briefly, the plasmid containing −168 to +21 of the murine aP2 promoter (BclI-PstI restriction fragment) was prepared by placing the −168 to +21 sequence upstream of the bacterial chloramphenicol acetyl transferase gene of the plasmid pUC-CAT.

Figure 1A:
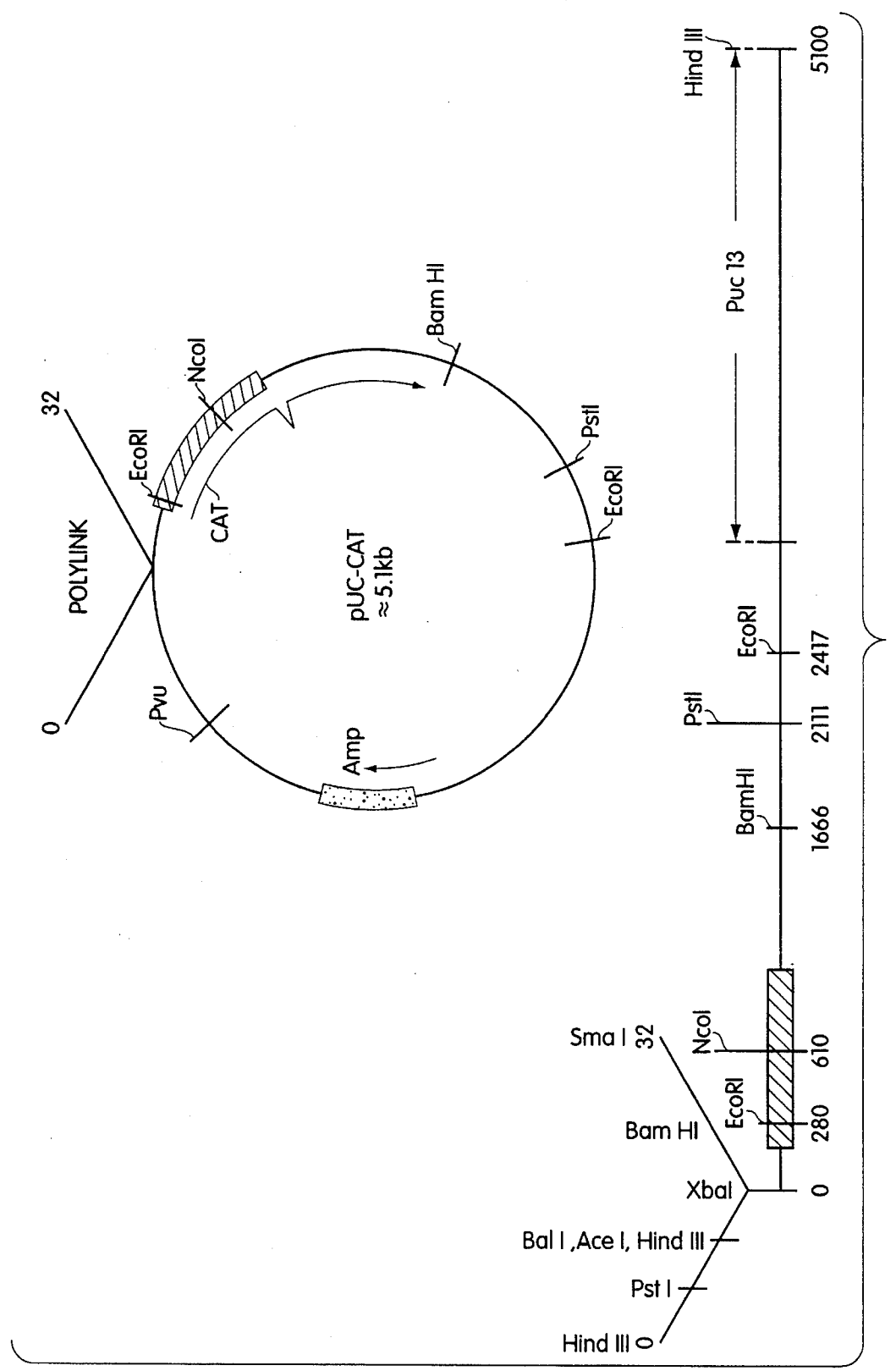
FIG. 1A is a map of the plasmid pUC-CAT, which has been used to demonstrate the tissue specificity of the adipose-specific DNA sequences of the present invention.
Figure 1B:
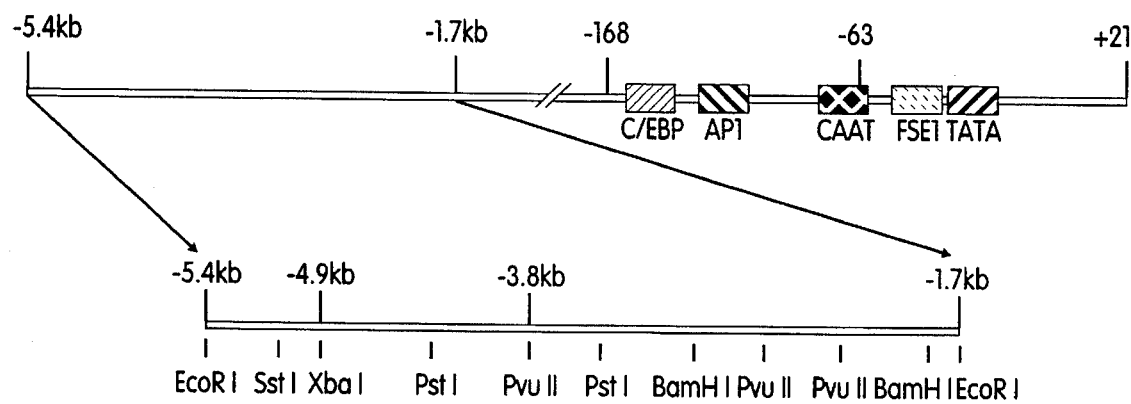
FIG. 1B is a restriction map of the 5' flanking region of the murine aP2 gene used to construct the transgenes described herein. The genomic DNA was obtained from genomic clone aP2911, the preparation of which has been described. Hunt et al., *Proc. Natl. Acad. Sci.*, 83:3786– 3790 (1986).

The pUC-CAT plasmid, which is illustrated in FIG. 1A, was prepared from the vector pUC13 (part of the Messing series of pUC plasmids) and includes an insert containing the CAT coding region and SV40 3' processing sites, i.e., the intron and polyadenylation signal sequence. The latter DNA was isolated from pSVOCAT, described in Gorman et al., *Mol. Cell Biol.*, 2:1044–51 (1982). The pUC13 vector was isolated as a SmaI and EcoRI cut fragment; the insert was prepared by cutting pSV0 with HindIII, converting the thus obtained fragment with SmaI and then partially digesting with EcoRI to release the appropriate fragment (Ca. 2.4 kb). The vector and the insert were then ligated together and the product pUC-CAT (ca. 5.1 kb) isolated. A 190 base pair (BclI-SmaI) fragment was inserted into pUC-CAT isolated as a 5.1 kb SmaI and partial Bam HI digestion.

The plasmid containing −247 to +21 of the murine aP2 promoter was prepared by placing the −247 to +21 PstI restriction fragment upstream of the CAT gene of the same PUC-CAT plasmid.

The −1.7aP2CAT transgene was prepared by ligating a −1.7 kb EcoRI to +21 bp PstI fragment of the aP2 gene into pUC-CAT. pUC-CAT was prepared for cloning by cutting with HindIII, filling in the ends with Klenow, partially digesting with PstI and then isolating the 5.1 kb vector. The −1.7 kb to +21 insert was obtained from the clone 4.1aP2.

(4.1aP2 was obtained by subcloning a 4.1 kb EcoRI fragment, isolated from the genomic phage clone aP2911, into pBS (Stratagene, LaJolla, Calif.). The 4.1 kb fragment contains the aP2 gene and −1.7 of 5' flanking region). The insert was obtained by cutting 4.1aP2 with EcoRI, filling in the ends with Klenow, cutting with PstI and then isolating the 1.7 kb promoter. The thus prepared vectors and inserts were then ligated and appropriate clones isolated. The resulting plasmid, −1.7aP2CAT, was about 6.8 kb, and exhibiting the following structure:

```
    −1.7kb       −168        +21
HindIII/EcoRI ... BclI ... PstISalIXbaIBamHISmaI-CAT-
SV40 ... pUC13 ... HindIII/EcoRI.
```

The / indicates that the two sites were joined by blunt end ligation of Klenow filled-in restriction sites.

−5.4aP2CAT was generated by first reconstructing the −5.4 kb to +21 aP2 promoter into Bluescript IISK+ (pSK, Stratagene, La Jolla, Calif.), releasing the insert as a SmaI to HindIII fragment and then inserting the thus released fragment into SmaI and HindIII cut pUC-CAT. Initially, the 1.7 kb EcoRI to PstI fragment from the aP2 genomic clone was inserted into EcoRI and PstI cut pSK to generate −1.7aP2. A 3.7 kb EcoRI fragment (−5.4 to −1.7 kb) from the same genomic clone was then inserted into EcoRI cut −1.7 aP2 and the correct orientation was isolated to generate −5.4 aP2pSK. The entire −5.4 kb to +21 fragment was then isolated as a HindIII to SmaI fragment from −5.4 pSK and inserted into HindIII and SmaI cut pUC-CAT to generate −5.4aP2CAT:

```
     −5.4        −1.7       +21
HindIIIEcoRVEcoRI ... EcoRI ... PstISmaI ... CAT ...
SV40 ... pUC13 ... HindIII
```

Generation Of Transgenic Mice

Transgenes containing either −168 to +21 (−168aP2CAT) or −247 to +21 (−247aP2CAT) base pairs of the promoter and 5' non-coding region linked to CAT sequences and the SV40 small t antigen splice and polyadenylation signals were purified from the plasmid vectors by restricting the plasmids and isolating the DNA fragments for microinjection from the bulk of the plasmid sequences either by extraction from low melting point agarose gels and/or by electroelution from standard agarose gels. For −168aP2CAT, a 2.4 kb fragment extending from SmaI to a PstI site was restricted from the plasmid, isolated and used for the injection. For −247aP2CAT, a 2.5 kb fragment extending from NsiI to PstI was used for the injection.

Transgenes −1.7aP2CAT (PstI-PstI, 3.9 kb) and −5.4aP2CAT (HindIII to NdeI −8.2 kb) were similarly prepared for micro-injection.

The linear fragments were then used for microinjection into Swiss Webster (SW) mice one-cell zygotes and implanted into pseudopregnant foster females as described by Choi et al., *J. of Virology*, 61:3013–3019 (October, 1987), the pertinent portions of which are incorporated by reference. In each instance, approximately 500 copies of the fragments in 5 picoliters were injected into each of about 300 eggs. SW mice were purchased from the NCI Frederick Animal Production Facility, Frederick, Md.

Approximately 75% of the microinjected eggs were implanted into the foster females, with between 20–40% ultimately resulting in offspring. Transgenes were identified, as described below, at a frequency of about 10–40% of the animals born.

Identification Of Transgenic Animals With CAT-Containing Transgenes

When the mice were weaned, total nucleic acids were extracted from a piece of the tail. To prepare genomic DNA from tissues, the tissue was homogenized in about 0.5 ml 1× PBS and then incubated with Proteinase K (Boehringer Manheim) at 50° C. for 12–16 hours. After digestion, cell debris was removed by centrifugation and the resulting supernatant containing the genomic DNA heated at 95° C. for five minutes to inactivate the Proteinase K. Centrifugation at 15,000 rpm for 10 minutes followed and 15 µl of the supernatant was used for PCR analysis. Positive transgenic animals with CAT-containing transgenes were identified by polymerase chain reaction, using primers that amplified a 280 bp fragment of the SV40 small t antigen splice/polyadenylation sequences. The two oligonucleotides used as primers were as follows:

5' $_{4201}$GACACTCTATGCCTGTGTGG$_{4220}$ [SEQ ID NO. 3]

and

3' $_{4476}$TGAGGCTACTGCTGACACAC$_{4441}$ [SEQ ID NO. 4]

wherein the subscript numbers refer to the SV40 genome.

The polymerase chain reaction was conducted on a COY Temp Cycler (35 cycles of denaturation, annealing and DNA synthesis) using standard techniques. Taq polymerase (ProMega Biotech, Wis.) was used to catalyze the extension of annealed oligonucleotide primers. The animals that gave positive signals are identified in Table 1 below.

CAT Assays

CAT activity was measured in extracts prepared from the tissue of the offspring of the $G_1$ and subsequent generations. The mice were sacrificed at about 8 weeks of age, and samples of liver, spleen, thymus, kidney, brain, skeletal muscle, lung, heart and white adipose tissue obtained. Extracts from the mouse tissues were prepared for CAT analysis by manually homogenizing the various tissues in 0.3–0.5 ml of 0.25M Tris-HCl (pH 8.0) and then sonicating the thus-prepared extracts in a water bath sonicator (Ultrasonics, Inc.) using 20 pulses of 50% power. After sonication, the extracts were centrifuged at 15,000 rpm for 10 minutes and the supernatant saved. The supernatant was heated at 65° C. for 6 minutes in order to inactivate deacetylase enzymes present in the tissues and recentrifuged. The supernatant obtained following centrifugation was used for the CAT activity assays.

CAT assays were carried according to Lopata et al., (1984) the pertinent portions of which are incorporated by reference. For all of the 168aP2CAT, 247aP2CAT, and 1.7aP2CAT transgenic tissues and for the tissues from the 5.4aP2CAT transgenic animals expressing low levels of CAT enzyme, approximately 200–300 µg of protein extract was assayed for 3 to 5 hours. In order to be within the linear range of the assay (<50% conversion of chloramphenicol to its acetylated forms), assays on extracts prepared from the fat, spleen and thymus of the 5.4aP2CAT mice were performed with 0.5 to 1 µg of protein for 30 min. to 1 hr. The assays were performed in a total volume of 175 µl containing 0.25M Tris-HCl (pH 8.0), 0.46 mM acetyl coenzyme A and 0.1 m Ci of $^{14}$C-labeled chloramphenicol (E. I. du Pont de Nemours and Co., Inc.). The reactions proceeded at 37° C. for 1–8 hours and were terminated by the addition of 1 ml of ethylacetate (J. T. Baker Chemical Co.). The samples were vortexed, centrifuged at 15,000 rpm for five minutes and the organic layer removed and dried under vacuum.

The dried material was resuspended in 25 μl of ethyl acetate and spotted onto a thin layer chromatography (TLC) sheet (J. T. Baker Chemical Co.). The chromatography was performed for about thirty minutes using a solvent composed of 95:5 chloroform:methanol. The chromatography sheets were exposed to Kodak X-Ray film without an intensifying screen.

The acetylated spots were cut out of the TLC and counted. Specific activities are presented either as cpm/mg protein/min reaction time or cpm/μg protein/min reaction time, depending on the activity of the extract.

The approximate copy number was determined by quantitative dot blot analysis. Quantitative DNA dot blot analysis was carried out by hybridizing dot blots of genomic DNA to a $^{32}$P-labelled CAT probe and scintillation counting the hybridized spots. Genomic DNA was prepared from mouse tissues by Proteinase K-SDS cell lysis followed by extraction with phenol/chloroform and ethanol precipitation. The ethanol precipitated DNA was resuspended in Tris-HCl (10 mM pH70-EDTA (1 ml) and 1 μg, 5 μg and 10 μg were used for dot blot analysis. Copy number was estimated by comparing the counts per minute (cpm) hybridized to a known amount of plasmid DNA.

The results of the foregoing experimentation are set forth in Table 1.

general, expression in all tissues was roughly proportional to copy number.

While the additional sequences in 1.7aP2CAT did not result in higher levels of CAT in adipose tissue, all four strains of transgenic animals containing the 5.4aP2CAT DNA expressed the transgene at very high levels in white and brown adipose tissue. See, Table 1. Three of the four transgenic strains (those that had ≦5 copies of the transgene had the highest levels of CAT activity in adipose tissue. None of the 5.4aP2CAT animals had appreciable activity in most other tissues, including liver as illustrated in Table 1. The addition of the 5' region from −1.7 kb to −5.4 kb not only increased the level of expression of the transgene in adipose tissue relative to other tissues, but boosted the overall level of expression in 5.4aP2 CAT mice by about 1000-fold. (The specific activities for the 168-, 268- and 1.7aP2CAT animals are given in cpm/mg protein, while those for the 5.4aP2CAT animals are given in cpm/μg protein in Table 1).

RNA Isolation And Analysis

Transcription of CAT in tissues was determined by extracting RNA from the tissues and assaying the RNA in a RNase T1 protein assay. RNA was isolated from tissues according to the method of Chirgwin et al., (1979). RNase T1 protection assays were carried out as previously

TABLE 1

CAT Activity In The Tissues Of aP2CAT Transgenic Mice

| Transgene[b] | Copy #[c] | Specific Activity In Tissues | | | | | | |
|---|---|---|---|---|---|---|---|---|
| | | Li | Sp | Th | Br | SM | Lu | Fa |
| 168aP2 14 | 50 | 0 | 33 | 17 | 1 | ND | 2 | 0 |
| 247aP2 2$_1$ | 675 | 12 | 5207 | 12,971 | 46 | 41 | 310 | 68 |
| 247aP2 2$_2$ | 5 | 7 | 33 | 17 | 1 | ND | 47 | 160 |
| 247aP2 3$_1$[a] | 1255 | 12 | 1351 | 3,295 | 305 | 107 | 51 | 70 |
| 247aP2 3$_1$[b] | 24 | 11 | 10 | 10 | 13 | 10 | 12 | 52 |
| 247aP2 3$_2$ | 21 | 0 | 9 | 12 | 24 | ND | 11 | 6 |
| 247aP2 5 | 45 | ND | 5 | 76 | 18 | 6 | 12 | 11 |
| 247aP2 10 | 15 | 0 | 33 | 55 | 7 | 2 | 57 | 20 |
| 1.7aP2 11 | 12 | 10 | 187 | 125 | 14 | 8 | 47 | 12 |
| 1.7aP2 3 | 5 | 0 | 456 | 241 | ND | 0 | 3 | 2 |
| 1.7aP2 6 | 45 | 4 | 814 | 402 | 6 | 3 | 7 | 34 |
| 1.7aP2 8 | 4 | ND | 484 | 1 | 425 | 0 | 19 | 8 |
| 5.4aP2 4[d] | 31 | 16 | 3800 | 730 | 12 | 120 | >440[e] | 280 |
| 5.4aP2 17[d] | 5 | 1 | 2200 | 4400 | 4 | ND | 1400 | >11,000[e] |
| 5.4aP2 18d | 5 | 8 | 450 | 360 | 29 | 43 | 73 | 860 |
| 5.4aP2 25d | <5 | 27 | 93 | 130 | 0 | ND | 43 | 1300 |

Abbreviations: Li, liver; Sp, spleen; Th, thymus; Ki, kidney; Br, brain; SM, skeletal muscle; Lu, lung; He, heart; Fa, white adipose tissue; ND, not determined.
[a]CAT specific activities are presented as cpm acetylated chloramphenicol/mg protein/ min. reaction time. Zero specific activity represents specific activities of <0.5.
[b]168aP2 contains the aP2 gene promoter from −168bp. 247aP2 begins at − 247bp, while 1.7aP2 begins at -1.7kb and 5.4aP2 begins at -5.4kb. All of these constructs extend to +21 at the 3' end.
[c]Approximate copy number was determined by quantitative dot blot analysis.
[d]CAT specific activity × 10$^3$ for these animals.
[e]CAT activity was in the non-linear range of the assay, so that accurate specific activities could not be determined.

As shown in Table 1, in the independently-generated strains of transgenic mice containing either of the 168aP2CAT or 247aP2CAT constructs, little or no CAT activity was detected in adipose tissue. This lack of expression was independent of transgene copy number. Even the adipose tissue from animals containing 1200 copies contained very low levels of CAT enzymatic activity. Moreover, significant expression was seen in several non-adipose tissues, such as the spleen, thymus, lung and brain, although liver CAT levels were very low or undetectable (Table 1; FIG. 2A). Southern blot analysis of DNA from these animals revealed no gross rearrangement of the transgenes and in described (Melton et al., 1984); the temperature of hybridization of the probes to the RNA were 37° C. for all probes containing CAT sequences, and 55° C. for probes containing adipsin sequences. Integrity of the RNA was checked by Northern blot analysis and hybridization to the housekeeping gene, glyceraldehyde phosphate dehydrogenase (Fort et al., 1985). The probe used for the detection of CAT RNA was generated by cloning a HindIII to EcoRI fragment from 5.4aP2 CAT into the HindIII/EcoRI site of a Gemini vector (ProMega).

RNase protection analysis of RNA isolated from the tissues of these mice reflected the CAT activity levels, indicating that the inclusion of the region from −1.7 kb to −5.4 kb resulted in increased mRNA levels derived from the transgene. Thus, sequences present in the aP2 gene between 1.7 kb and 5.4 kb upstream from the transcription start site enhanced expression dramatically in adipose tissue.

EXAMPLE 2

This example demonstrates that the enhancement of expression obtained with the −1.7 kb to −5.4 kb construct was independent of the attached marker gene, CAT.

Figure 1C:
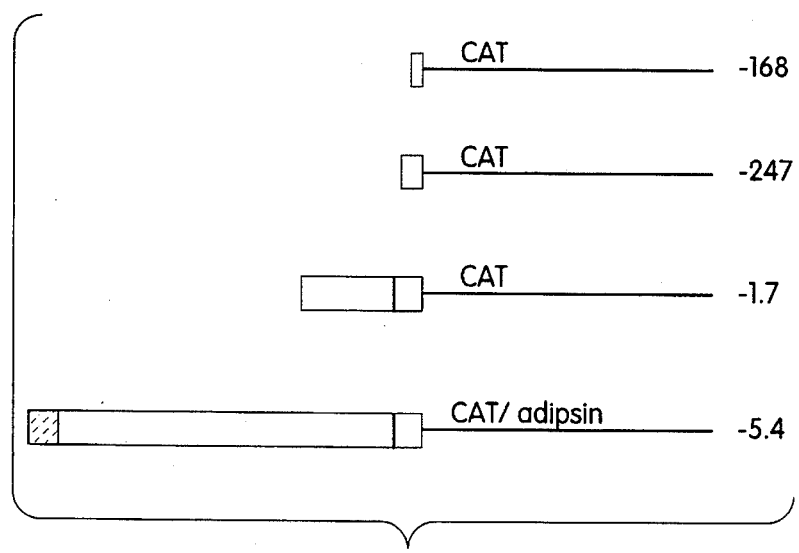
FIG. 1C is a representation of the −168aP2, −247aP2, −1.7aP2 and −5.4aP2 constructs used to make transgenic mice. The open boxes represent aP2 sequences; the lines, CAT/SV40 sequences. The putative glucocorticoid regulatory element at −363 nucleotides is represented by a solid bar, while the 518 base pair sequence containing the 5' adipose-specific enhancer is represented by a hatched box.

The results described in Example 1 indicate that sequences within the 5' flanking region of the murine aP2 gene cause high levels of expression of linked genes in adipose tissue. To show that this enhancement of expression was independent of the linked marker gene and not the result of an interaction between the CAT/SV40 marker gene and aP2 sequences, another transgene, 5.4aP2adn was constructed. This construct contained the same −5.4 kb to +21 of the aP2 gene linked to a hybrid cDNA/genomic adipsin gene and is illustrated in FIG. 1C.

The construct was prepared by ligating a 500 bp BamHI to BstEII (codon 167) cDNA fragment from the adipsin vector pMTpn-Adn (Rosen et al., *Science*, 244:1483–87 (1987) containing the AUG codon to a 4.8 kb BstEII-EcoRI genome fragment containing the UGA stop codon and 4 kb of 3' flanking sequences from lambda -ADN genomic clone. (Min and Spiegelman, *Nucleic Acids Res.*, 14:8879–92, 1986). The aP2 5.4 kb to +21 bp fragment (EcoRI-PstI) was then ligated upstream of the adipsin sequences.

The 5.4aP2ADN vector was then used to generate transgenic animals, in accordance with the experimental protocol described in Example 1. A 10.1 kb fragment (HindIII to PvuI) was used in the microinjection.

Seven strains of transgenic mice containing this transgene were produced and expression in various tissues was examined using an RNase T1 protection assay. RNA was extracted from various tissues, including the spleen, brown fat and fat, in accordance with the method of Chirgwin, *Biochemistry*, 18: 5294–99 (1979) and RNAase T1 protection assays were carried out as previously described (Melton et al., *Nucleic Acid Res.*, 12: 7035–7056, 1984)). In this experiment, a 430bp fragment from the junction between the aP2 and adipsin sequences was cloned into the Bluescript (Stratagene, Calif.) vector and used to make a 475 bp probe. The temperature of hybridization of the probes to the RNA were 55° C. for all probes containing the adipsin sequences. The integrity of the RNA was checked by Northern blot analysis and hybridization to the housekeeping gene, glyceraldehyde phosphate dehydrogenase (Fort et al., *Nucleic Acid Res.*, 13: 1431–1442 (1985).

As shown in FIG. 3, transcription from the transgene (detected as a 406 nt band), and the endogenous adipsin gene (detected as bands of 352 nt and 276 nt), was found in both white and brown adipose tissue, while both were undetected in other tissues, such as spleen. This result was reproducible for all of the 5.4aP2adn transgenic mice examined.

These experiments show that the regulation of gene expression by the 5.4 kb flanking region of the aP2 gene acts at the RNA level and that initiation occurs at the appropriate transcription start site. Moreover, results of the experimentation demonstrate that the aP2 promoter construct is clearly capable of enhancing the expression of different linked genes.

EXAMPLE 3

This example demonstrates that the aP2 adipocyte specific enhancer element maps to the 5' distal end of the 5.4 kb fragment isolated in Example 1 and is the primary determinant of tissue-specific expression of this gene.

To more precisely map the enhancer element in the aP2 gene between −1.7 kb and −5.4 kb, transient transfections with a variety of constructs into undifferentiated and differentiated 3T3-F442A adipose cells were carried out. A basal promoter, −63 aP2CAT (referred to as −64aP2CAT in Distel et al., 1987) was used, because this construct is inactive in both cell types and is deleted for the proximal regulatory elements (C/EBP, AP-1 and CCAAT box. (Distel et al., *Cell*, 49:835–844 (1987); Rauscher et al., *Cell*, 52:471–80 (1988)).

Preparation of constructs

Plasmid −63 aP2CAT, described by Distel et al., (*Cell*, 49:835–44 (1987)) includes a DNA sequence encoding CAT which is operatively associated with a basal promoter from murine aP2, comprising nucleotides −63 to +21 (neclleotides 52–134 of SEQ ID BO.2. (− 63 aP2CAT is described as −64aP2CAT by Distel et al., and was obtained as a 5' deletion of the −168aP2CAT construct.) A series of restriction fragments from the 5' flanking region of the murine aP2 gene were inserted at the HindIII site of the −63 aP2CAT vector, thereby placing the fragments upstream of the basal aP2 promoter. The restriction fragments inserted included a −5.4 to 1.7kb (EcoRI-EcoRI) restriction fragment, −5.4 to −3.8 kb (EcoRI-Pvu 11) restriction fragment and a −5.4 kb to −4.9 kb (EcoRI-XbaI) restriction fragment from the 5' flanking region of the aP2 gene. See, FIG. 1B. Deletion constructs of the 5.4 kb to 1.7 kb fragments were made by blunt end ligation of the various restriction fragments into HindIII restricted and Klenow filled in −63 aP2CAT. The origin and orientation of the DNA fragments inserted at the HindIII site of the basal −63 aP2CAT vector are indicated in FIG. 4. The thus-prepared aP2CAT fusion plasmids were then transferred into 3T3-F442A preadipocytes and adipocytes.

Cell Culture And Transfection

3T3-F442A preadipocytes and adipocytes were cultured as previously described. (Wilkison, et al., *J. Biol. Chem.*, 265: 477–482 (1990) and Cook et al., *Proc. Natl. Acad. Sci.*, 82: 6480–6484 (1985)). Transfections were done at day 2 after confluence in preadipocytes and days 4–6 after confluence in adipocytes. For transfections, 20 µg of plasmid DNA was mixed with 5 ml of Dulbecco's medium containing 50 mM Tris-HCl, pH 7.3 and either 100 µg/ml DEAE dextran for preadipocytes or 250 µg/ml DEAE dextran for adipocytes. The cells were incubated for 3 hours at 37° C., then the cells were shocked with 10% DMSO in PBS for 3 min. at 37° C. The monolayers were washed again with PBS, then incubated with serum-containing medium for 48 hours.

Assay For CAT Activity

CAT assays were done essentially by the method of Gorman et al., *Mol. Cell Biol.*, 2: 1044–51 (1982) with minor modifications. First, the cell extracts were prepared by freezing and thawing cell pellets instead of sonicating. Second, the cell extracts were heated to 60° C. for 7 min. to inactivate endogenous deacetylases. Third, the acetyl-CoA concentration in the assay was increased from 0.4 to 2.4 mM to ensure linearity. The reactions were incubated at 37° C. for 4 hours and stopped by the addition of 1 ml of ethyl acetate. Quantitation of CAT activity was done by cutting out spots from the silica gel containing the $^{14}$C-labeled acetylated and unacetylated chloramphenicol and counting in scintillation fluid.

As shown in FIG. 4, transfected plasmids containing from −5.4 kb at the 5' end to either −1.7 kb, −3.8 kb, or − 4.9 kb at the 3' end of the fragment (FIG. 1B) ligated upstream of −63 bp in the aP2 promoter, stimulated higher levels of CAT expression in adipocytes, relative to the expression seen from the basal 63aP2CAT construct. The plasmid containing the −4.9 kb to −3.8 kb region ligated upstream of this same promoter/CAT sequences showed no enhancement of expression.

The EcoRI to XbaI restriction fragment mapping between −5.4 kb and −4.9 kb, when linked to the minimal aP2 promoter, did not significantly enhance expression in preadipocytes, indicating that its enhancing function was differentiation-dependent.

Generation of Transgenic Animals

To determine if the region between −4.9 kb and −5.4 kb also functioned as an enhancer in animals, transgenic mice containing this restriction fragment (linked upstream of the aP2 promoter at −63 bp) were constructed and CAT activity in various tissues was measured.

The −4.9 kb to −5.4 kb vector (termed 518aP2CAT) was prepared for microinjection into mouse eggs by restricting the vector with AluI and NdeI.

A 4 kb AluI-NdeI fragment was then separated from the bulk plasmid fragments on an agarose gel and used for injection into eggs. Swiss Webster one-cell zygotes (≈300) were injected, as in Example 1, with 5 picoliters containing about 500 copies of the fragment and implanted into pseudo-foster females as described. 56 animals developed from the eggs, and the animals were detected for the presence of the transgene, as described in Example 1. Tissue samples were analyzed for CAT activity, as previously described.

Three of the animals expressed the transgene and, as shown in Table 2 below, the 518aP2CAT construct functioned in a fat-specific manner. Adipose tissue contained from 3– 50 fold higher levels of CAT activity than any other tissue in the animal, depending on the transgenic strain. This degree of adipocyte-specificity is generally consistent with the tissue-specific expression of the endogenous gene (Bernlohr et al., *Biochem. Biophys. Res. Comm.*, 132: 850–855 (1985); Zezulak and Green, *Mol. Cell Biol.*, 5: 419–421 (1985)). As was seen with the 5.4aP2CAT mice, transgene expression was orders of magnitude higher in the 518aP2CAT animals relative to the levels seen in transgenic animals lacking the enhancer sequence.

TABLE 2

| Transgene | Copy #[b] | CAT Specific Activities in Tissues[a] | | | | | | |
|---|---|---|---|---|---|---|---|---|
| | | Li | Sp | Th | Br | SM | Lu | Fa |
| 518aP2 2[c] | 10 | 26 | 1 | 17 | 0 | 4.2 | 1 | 1235 |
| 518aP2 6 | 25 | 52 | 0 | 37 | 0 | 158 | 0 | 598 |
| 518aP2 11 | 5 | 25 | 166 | 195 | 57 | 178 | 0 | 9065 |

The 518aP2 construct contains from −5.4kb to −4.9kb in an inverted orientation ligated to the −63bp to +21bp fragment of the aP2 gene.
[a,b,c]See legend for Table 1.

RNAase Protection Assay

Since the 518aP2CAT molecule contained only a small region of the promoter, it was possible that the CAT activity that was detected in the adipose or other tissues of transgenic mice containing this construct was due to initiation at novel sites formed by the juxtaposition of sequences within the 518 bp fragment and the promoter. RNAase T1 protection assays were therefore carried out using a probe that spanned the junction between the aP2 and CAT sequences. The results showed that RNA transcription initiated at the normal aP2 start site in the adipose tissue of strain 518aP2CAT 2 transgenic mice, resulting in protection of a fragment of 294 nt. CAT transcripts were detected only in the adipose tissue of the 518aP2CAT mice, which reflects the lower levels of transgene expression in the other tissues.

Sequencing

The sequence of the 518 base pair aP2 adipose-specific enhancer element is set forth in SEQ ID NO: 1. The sequence was determined by dideoxy sequencing using the sequenase kit from USBIOCHEMICAL of Cleveland, Ohio. For sequencing −5.4 to −4.9, the EcoRI to XbaI fragment was inserted into pBs' and M13 primers used for sequencing.

EXAMPLE 4

This example describes the preparation of deletion constructs of the 518aP2CAT transgene which retain the ability to deliver genetic material specifically to adipose tissue in culture.

Various restriction enzymes were used to cleave the 518 base pair aP2 enhancer sequence into three smaller fragments containing DNA from −5.4 to −5.0 kb, −5.4 to −5.2 kb and −5.2 to −5.0 kb. The restriction enzyme sites are indicated in FIG. 1B. The SstI site generated a 380 bp fragment (−5.4 to −5.0 kb), which was then cleaved in half with Sau3AI to generate the fragments from −5.4 to −5.2 kb and from −5.2 kb to −5.0 kb. These fragments were then ligated to the −63aP2CAT construct as previously described and transiently transfected by DEAE-dextran adsorption with 20 μg of plasmid DNA. CAT activity was assayed as described in the previous Examples herein.

The results of this experiment showed that when linked to the −63aP2 construct, the −5.4 to −5.0 fragment had similar activity to the 518 bp fragment (−5.4 to −4.9 kb). When this fragment (−5.4 to −5.0 kb) was cleaved with Sau3AI, the 5' half (−5.4 to −5.2 retained enhancing activity while the 3' half had no detectable activity.

The three fragments can be used to generate transgenic mice in accordance with the procedure described herein, to determine whether the −5.4 to −5.0 and −5.4 to −5.2 kb fragments are sufficient to direct adipose-specific expression of a heterologous gene in vivo.

EXAMPLE 5

In Example 4, it was demonstrated that an approximately 180 base pair fragment (an EcoRI-Sau3AI fragment extending from about −5.4 to −5.2 kb), at the 5' end of the aP2 enhancer sequence can stimulate promoter activity in cultured adipocytes, however the cell type specificity of this fragment was not explored. This Example describes the identification of an adipose regulatory element (ARE) located within the murine aP2 enhancer sequence, and more specifically within the most 5' end of the enhancer, that binds a trans-acting nuclear factor(s) that appears to provide the differentiation dependent switch for tissue-specific expression of the aP2 enhancer. When used alone or in concatenated form, DNA sequences containing these ARE's and the nuclear factor(s) which binds to the multimerized sequence in a differentiation dependent manner, can be used in screening assays to identify organic molecules that interfere with the nuclear protein binding. Molecules identified in this fashion are potentially useful as therapeutic reagents in the treatment of adipose-related disorders, particularly obesity.

All references herein to base pair numbers refer to the bases of the murine aP2 enhancer element as set forth in SEQ ID NO:1.

A NlaIII-Sau3AI Restriction Fragment of the aP2 Enhancer Is Capable of Conferring Adipose Differentiation-Dependent Activity.

The −5.4 to −5.2 kb, EcoRI-Sau3AI restriction fragment at the 5' end of the aP2 enhancer and two shorter restriction endonuclease fragments derived from it, as illustrated in FIG. 10, were tested for their ability to stimulate CAT gene expression from the enhancerless SV40 promoter in a reporter vector, pSVKSI, when transfected into cultured preadipocytes or adipocytes. The pSVKSI vector is illustrated in FIG. 11; however, any suitable vector including the CAT gene and a suitable promoter, could alternatively be employed.

Transfections were carried out in preadipocytes and adipocytes as previously described, except that transfections were carried out using coprecipitates of calcium phosphate and DNA rather than by the DEAE-dextran methodology. Calcium phosphate medium transfection has now been determined to be the preferred method for introducing DNA into adipose cells in accordance with the invention.

For transfections, adipocyte and preadipocyte cells were washed with 5 ml of phosphate buffered saline containing 1 mM EDTA 2–4 hours prior to transfection. Cells were then refed with 10 ml of media. DNA-CaPO$_4$ phosphate precipitation were carried out in accordance with Sambrook, Fritsch and Maniatis, *Molecular Cloning*, §16.33 (1989). The exact method for precipitate formation is not critical and can be accomplished via any of the known modifications without significantly altering the result. The reaction was then carried out substantially as set forth in Maniatis, with the specific modifications noted below. After transfer to cell monolayers, the precipitate was left on the cells for 3–4 hours.

Following incubation, the media and precipitate were removed by aspiration and 6 ml of phosphate buffered saline containing 10% glycerol was added to the cells. The glycerol solution was left on cells for about 3 minutes at 37° C., then removed and washed in PBS and refed with 10 ml of complete growth media.

Cells were left overnight, refed again with 10 ml of complete growth media and harvested the following morning and assayed from transient transfection as described.

All transfections were performed in duplicate and normalized to an internal control of a cotransfected mtHGH gene.

The results of these transfections, summarized in FIG. 10, revealed that all three fragments were able to stimulate promoter activity only in differentiated adipocytes. While deletion of approximately the first 48 base pairs of the enhancer sequence had no effect on enhancer activity, CAT gene expression was significantly reduced (≈50%) when sequences from about 49 bp to about 65 were deleted by cleavage with NlaIII. This region of the aP2 enhancer, i.e. ≈bp 49–65, contains the adipose regulatory element, ARE1, that binds a member of the NF1 family and has previously been shown by mutational analysis to contribute to the enhancing activity of the aP2 enhancer. Graves et al., *Genes & Development*, 5:482–437 (1991). Nevertheless, the results clearly showed that the NlaIII-Sau3AI fragment was capable of conferring adipocyte differentiation-dependent activity on the SV40 early promoter.

DNase Protection Analysis And Mobility Shift Assay

Since the NlaIII-SauSAI fragment located near the 5' end of aP2 enhancer exhibited the ability to direct gene expression in a differentiation-dependent manner in adipocytes, the fragment was further analyzed in order to identify key cis- and trans-acting components responsible for developmental regulation. DNase protection analysis of the fragment was carried out following the protocol described in *Current Protocols In Molecular Biology*, §12.4, and revealed a prominent footprint extending from about bp 114 to 146 of the aP2 enhancer SEQ ID NO 15. This sequence is hereinafter referred to as ARE2.

The binding of nuclear proteins to a double-stranded oligonucleotide spanning this ARE2 region was assessed using several oligonucleotides as competitors by electrophoretic DNA mobility shift binding assays. The important regions of the competitive oligonucleotides used in the mobility shift assays are reproduced in FIG. 12. All synthetic oligonucleotides were prepared by Midland Certified Reagent Company, (Midland, Tex.) and used without further purification. Mutations was made using the Amersham mutagenesis kit in accordance with the manufacturer's instructions.

Nuclear extracts for the experiments were prepared from preadipocytes and adipocytes according to the method of Shapiro et al., *DNA*, 7(1):47–55 (1988), using 3T3-F442A preadipocytes and adipocytes, which had been cultured as described in Example 2. Final protein concentrations were typically about 20–30 µg/ml.

DNA mobility shift assays were conducted in accordance with a modification of the procedure described by Distel et al., *Cell*, 49:835–844 (Jun. 19, 1987). DNA binding was conducted in 20 µl incubations. Nuclear extract (1–3 µl) was incubated with 1 µg of poly(dI-dC) (Boeheringer Mannheim) and 2 picomoles of double-stranded non-specific oligonucleotides in binding buffer (10 mM Tris-HCl [pH 7.5], 50 mM NaCl, 5% glycerol, 5.0 mM MgCl$_2$, and 1.0 mM EDTA) for 15 minutes at room temperature. Restriction fragments or synthetic nucleotides were end-labeled by filling in the 3' recessed ends with one or more [alpha-$^{32}$P] dNTPs, using the large fragment of *E. coli* PolI (Klenow fragment) (Maniatis et al., *Molecular cloning*, 1989). Approximately 20 fmoles of $^{32}$P-labeled DNA (<40,000 cpm) was added to the preincubated nuclear extract, which was then incubated for 15 minutes. For competition assays, competitor DNA's were added at the same time the labeled fragment was added, in an amount of about 1–2 picomoles. DNA-protein complexes were resolved on polyacrylamide gels (30:1 acrylamide to bisacrylamide) in 0.5× TBE (1× TBE, 50 mM Tris-borate [pH 8.3], 1 mM EDTA). The gels were dried and autoradiographed with intensifying screens (duPont) at −70° C.

The results showed that a prominent DNA-protein complex was formed after incubation of ARE2 DNA with either preadipocyte or adipocyte nuclear extracts. Assessment of sequence-specificity of complex formation using the competitor oligonucleotides revealed that the cognate ARE2 oligonucleotide was able to compete for binding of the protein, whereas an oligonucleotide containing a three base mutation in the ARE2 sequence (ARE2M1 in FIG. 12) as well as an oligonucleotide containing the consensus binding site for the CAAT/Enhancer Binding Protein (C/EBP) were not able to compete.

By DNA sequence comparison, an additional region of the 518bp aP2 enhancer were identified as potential binding sites for the factor binding to ARE 2. This region, referred to as ARE4, extends from about bp 196 to 220 and was an effective competitor for nuclear protein binding to ARE2.

The ARE2 and ARE4 Binding Cites Fail To Confer Differentiation-Dependent Promoter Activity The role of the two binding sites, ARE2 and ARE4 in the aP2 enhancer was evaluated in functional assays as follows. First, double-stranded, ARE2-containing oligonucleotides were multimerized (three copies in tandem) and inserted in inverse orientation into the pSVKSI CAT vector.

Oligonucleotides were multimerized by ligation in accordance with established protocols, (see e.g. Sambrook et a, §12.30 et seq, previously cited) and then inserted into PVKS1 by blunt end ligation in accordance with standard procedures. Enhancing activity was assayed following transient transfection into cultured cells as previously described.

The results of this experimentation showed that the multimerized ARE2 oligomers were capable of significant stimulation of promoter function. However, the activity was not differentiation-dependent, since equivalent stimulation was observed in both preadipocytes and adipocytes.

Next, ARE2 and ARE4 sites were mutated independently in the context of the 518 base pair aP2 enhancer and the resulting constructs were assayed for activity by transient transfection. Both of the mutations severely reduced enhancer function as detected by the reduction in CAT activity in adipocytes; however, some residual activity was observed. The residual activity was differentiation-dependent and was also observed when the ARE2 mutation was assayed in the context of the smaller NlaIII-Sau3AI fragment.

Differentiation-Dependent Activity Is Conferred By aP2 Sequences That Bind a Nuclear Protein Present In Adipocyte, But Not Preadipocyte, Nuclear Extracts The foregoing data suggested that other cis-acting elements in addition to ARE2 contribute to the activity of the NlaIII-Sau3AI fragment of the aP2 enhancer sequence and particularly to its cell-type specificity. To identify this element(s), two additional synthetically prepared oligonucleotides were purchased from the Midland Certified Reagent Company, Midland, Tex.:

Oligonucleotide X, containing bp 61 to 116 of the 518 bp aP2 enhancer [SEQ ID NO.1]; and Oligonucleotide Z, containing bp 138 to 181 of the 518 bp aP2 enhancer [SEQ ID NO.1].

These fragments, together with the ARE2-containing oligonucleotide (bp 146–162) spanned most of the ≈120 bp NlaIII-Sau3AI fragment. The X and Z oligonucleotides were multimerized in tandem in reverse orientation as described above and inserted into the pSVKSI-CAT vector. Both constructs were then tested for their ability to stimulate differentiation-dependent gene expression by transient transfection into cultured cells as previously described.

As shown in FIG. 13, unlike multimers of the ARE2 sequence, multimers of both oligonucleotides X and Z were capable of stimulating promoter activity only in differentiated adipocytes; no activity from either construct was seen in the transient transfection of preadipocyte cells in culture. As controls, constructs containing the NlaIII-Sau 3AI fragment and constructs driven by the Rous sarcoma virus LTR promoter were also transfected into cultured cells.

Since both the X and Z oligonucleotides were capable of directing differentiation-dependent gene expression, the sequences of the two oligonucleotides were compared. The comparison revealed a region with a 10 out of 12 bp identity, designated ARE6 (bp 93 to 104 on the coding strand illustrated in SEQ ID NO:1) and ARE7 (bp 180 to 169 on the non-coding strand. The sequence comparisons are set forth in FIG. 14A. See also SEQ. ID. NOS. 8 and 9.

ARE6 and ARE7 Appear To Bind The Same Protein Factor In Adipocyte Nuclear Extract The pattern of protein binding to the ARE6 and ARE7 motifs and flanking regions of the aP2 enhancer was investigated by electrophoretic DNA mobility shift binding assays as described above. Briefly, double-stranded oligonucleotide containing an ARE6 binding site was radiolabeled and then incubated with nuclear protein extracted from adipocytes and the DNA-protein complexes were resolved from free DNA by electrophoresis on polyacrylamide gels. Sequence specificity of protein binding was assessed by inclusion of a 50 molar excess of various oligonucleotides, including two oligonucleotides containing a mutation in the ARE6 site (ARE6M1 and ARE6M2), and ARE2-containing oligonucleotide and ARE7-containing oligonucleotide. Oligonucleotides used were:

ARE6 5'-TCGGCGCACATTTCACCCAGAGAGAAGGGATTG-3' SEQ ID NO 12

ARE6M1 5'-GCACATTTCACCCATCTAGAAGGGATTG-3' SEQ ID NO 13

ARE6M2 5'-GCACATTTCCTGCAGAGAGAAGGG-3' SEQ ID NO 14

ARE2 5'-CAGCAGGAAGTCACCACCCAGAGAGCAAATGGA-3' SEQ ID NO 15 [nucleotides 6–146 of SEQ ID NO1]

ARE7 5'-CAAATGGAGTTCCCAGATGCCTGA-CATTTGCCTTCTTACTG SEQ ID NO 16

The results of these experiments revealed that adipocyte nuclear extracts contain a sequence-specific DNA binding protein that recognizes the ARE6-containing oligonucleotide (FIG. 14B). This binding was competed by either the cognate oligonucleotide (ARE6) or an oligonucleotide containing an ARE7 site (FIG. 14B, lanes 2 and 7). Oligonucleotides that contained a mutation in the ARE6 site (ARE6M1 and ARE6M2) were unable to compete for binding of the adipocyte extract nuclear factor, as also shown in FIG. 14B.

Proteins That Bind ARE6 Are Found Only In Differentiated Adipocytes

Since the function of ARE6 was differentiation dependent, an investigation was conducted to determined whether the protein(s) that bind to the ARE6 site are found only in differentiated cells. Nuclear extracts, derived as described above from different cells types, including two preparations from a preadipocyte cell line (3T3F44A preadipocyte preparations 1 and 2), 3T3C2, C2C12 and HeLa cells, were prepared and used as the source of DNA binding proteins in mobility shift assays. As demonstrated in FIG. 14C, sequence-specific binding to the ARE6-containing oligonucleotide was observed only with adipocyte nuclear extract. This experiment was performed with several different preparations of preadipocyte extract and also with varying amounts of extract and in each instance, no binding has been detected in undifferentiated cell extracts.

Finally, the effect of two independent mutations of the ARE6 site in the context of the entire 518 bp enhancer was assayed. The ARE6 site in the 518 bp enhancer was mutated by oligonucleotide-directed mutagenesis using the oligonucleotides ARE6M1 and ARE6M2 shown above. The mutated enhancer was then inserted into pSVKSlCAT and the constructs separately transiently transfected into adipocytes. The level of CAT gens expression was determined by measuring CAT enzyme activity as previously described.

Each of the mutations ARE6M1 and ARE6M2 severely abrogated enhancer activity in adipocytes, as illustrated in Table 1 below. In contrast, neither mutation had any effect on the minimal level of enhancer activity in preadipocytes, i.e., there was no activation of the enhancer by mutation.

TABLE 2

| CAT Constructs | % Maximal Activity |
| --- | --- |
| 520 WT | ≈100% |
| 520 ARE6 M1 | 13.8% |
| 520 ARE6 M2 | 7.9% |

EXAMPLE 6

It has previously been shown that the first 1000 base pairs 5' of the transcription start site of the adipsin gene are sufficient to direct expression of genetic material in cultured adipocytes. This example describes the isolation of the promoter region from the murine adipsin gene which positively regulates expression in fat tissue in vivo.

Preparation of ADN-CAT Fusion Genes

The adipsin-CAT fusion plasmids were prepared using the pAE5 CAT vector (Spiegelman et al., *J. Biol. Chem.*, 258: 10083–10089 (1983)) and adipsin sequences from lambda-ADN (Min and Spiegelman, *Nucleic Acids Res.*, 14:8879–8892 (1986)). The pAE5 vector was derived from the plasmid pSVlxCAT-AB3 (Celander et al., *Nature*, 312, 159–162 (1984)) and contains a mutant SV40 early promoter region between XhoI and HindIII sites of the CAT gene and the Akv viral enhancer (−443 and −110 of the Akv lung terminal repeat, Van Beveren et al., *J. Virol.*, 41: 542 (1983)) 3' of the CAT gene at the BglII site of pSVlxCAT-AB3.

The pADN (−950) vector was prepared by excising the XhoI-HindIII SV40 promoter fragment of pAE5 and replacing it with a BamHI-RsaI fragment spanning 0.95 kilobases of the 5' flanking downstream to 35 bp 3' of the transcription start site of the adipsin gene. A similar plasmid containing an XbaI-RsaI fragment of approximately 700 bp of the 5' flanking sequence (pADN-CAT (−700)) was also constructed. Subsequent 5' deletions of the adipsin upstream region were made from (pADN-CAT (−700)) by linearizing it with XhoI and then digesting for various times with Bal 31 nuclease. The deleted ends were repaired with T4 polymerase and XhoI linkers attached. The 5' deleted fragments were excised with HindIII and then ligated into the pAE5 vector minus the XhoI-HindIII promoter fragment. The 5' ends of all deletions were identified by DNA sequencing of plasmids. The following deletion plasmids were prepared in accordance with the foregoing: pADN-CAT (−344); pADN-CAT (−305); pADN-CAT (−284); pADN-CAT (−250); pADN-CAT (−215); pADN-CAT (−114); and pADN-CAT (−38).

Cell Culture and Transfections

The thus-prepared plasmids were then transfected into 3T3-F442A preadipocytes and adipocytes to delineate the regions within the adipsin promoter which direct differentiation dependent gene expression in vivo. Cell cultures and transfections were carried out as described in Example 3, except that transfections were conducted with 10 µg of each plasmid.

Assays for CAT Activity

CAT assays were done essentially by the method of Gorman et al., *Mol. Cell Biol.*, 2: 1044–1051 (1982) with some modifications. First, the cell extracts were prepared by freezing and thawing cell pellets instead of sonicating. Second, the cell extracts were heated to 60° C. for 7 min. to inactivate endogenous deacetylases (Mercola et al., *Science*, 227: 266–70 (1985)). Third, the acetyl-CoA concentration in the assay was increased from 0.4 to 2.4 mM to ensure linearity. The reactions were incubated at 37° C. for 4 hours and stopped by the addition of 1 ml of ethyl acetate. Quantitation of CAT activity was done by cutting out spots from the silica gel containing the $^{14}$C-labeled acetylated and unacetylated chloramphenicol and counting in scintillation fluid.

The results of the CAT assays of cell extracts of the pADA-CAT (−950) transfection and variations are set forth in FIG. 6. As illustrated in FIG. 6, upon transfection with pADN-CAT (−950), preadipocyte extracts exhibited only background CAT activity, whereas adipocyte extracts showed significant CAT activity above background. No CAT activity was observed in mock transfection lacking plasmid DNA or in transfections with pADN-CAT (−950)F in which the 985-bp adipsin 5'-flanking region was in an inverted (3' to 5') orientation upstream of the CAT gene. A positive control used for transfection efficiency, the original PAE5 vector, exhibited abundant CAT expression in both preadipocytes and adipocytes. This plasmid contains SV40 promoter sequences upstream of the CAT coding region and the Akv enhancer downstream of the CAT gene. This vector also demonstrated that the Akv enhancer in the pADN-CAT construction does not exhibit inherent differentiation-dependent activity since CAT activity in adipocytes transfected with the pAE5 vector was similar to that observed in preadipocytes. Thus, these experiments strongly suggest that the adipsin gene contains sufficient regulatory information within 950 bp of the 5'-flanking sequence to direct differentiation-dependent expression of a heterologous gene in fat cells.

The transfections with the 5' deletions of pADN-CAT allowed a more precise delineation of the regions within the adipsin promoter responsible for directing differentiation-dependent expression. The CAT activity of the pADN-CAT (−700) deletions are set forth in Table 3 below.

TABLE 3

| | CAT Activity | |
|---|---|---|
| Plasmid | Preadipocyte % conversion | Adipocyte to acetylated forms |
| pAU3CAT | 7.0 (1.00) | 12.9 (1.00) |
| pADN-CAT (−344) | <0.1 (0.01) | 5.6 (0.43) |
| pADN-CAT (−305) | <0.1 (<0.01) | 10.1 (0.79) |
| pADN-CAT (−284) | <0.1 (0.01) | 3.9 (0.33) |
| pADN-CAT (−250) | <0.1 (0.01) | 5.0 (0.39) |
| pADN-CAT (−215) | <0.1 (0.01) | 8.5 (0.66) |
| pADN-CAT (−114) | <0.1 (0.01) | 9.8 (0.76) |
| pADN-CAT (−38) | 2.3 (0.32) | 0.8 (0.06) |

In Table 3, the base number refers to the 5' boundary of adipsin sequences, as determined by sequencing. Preadipocytes and adipocytes were transfected with DEAE-dextran and 2 µg of pAU3CAT, a positive control vector (Celander et al., *Nature*, 312: 159–162, (1984)), or 10µg of other plasmids. CAT activity was determined as described. Background counts from mock transfections were subtracted from all data. The numbers in the parentheses present data normalized to pAU3CAT, which is given as 1.00. The increase in CAT activity in preadipocytes and the decrease in adipocytes between the −114 and −38 deletions were observed in at least 15 separate transfections with six different plasmid DNA preparations and were also observed in pooled stable transfectants.

Deletions from −950 to −344 caused no significant change in CAT activity in extracts of preadipocytes or fat cells (not shown). The data in Table 3 illustrate that further deletions from −344 toward the transcription start site caused only small changes in CAT expression until the deletions reached the region from −114 to −38 (Table 3). In preadipocytes, CAT activity markedly increased (at least 20-fold) above the background level when the region from −114 to −38 was deleted, suggesting that one or more negative regulatory elements had been lost. In adipocytes, deletion to −38 caused a dramatic (>9-fold) drop in CAT expression, suggesting that there was an element between positions −114 and −38 which positively regulated expression from the adipsin promoter in these cells. The rise in CAT activity in preadipocytes and the drop in activity in fat cells which occurred upon deletion from −114 to −38 were both highly reproducible.

Generation of Transgenic Animals

The foregoing experiment demonstrated that constructions comprising a −114 to +35 segment of the adipsin promoter are preferentially expressed in adipose cells in culture. In order to determine whether the same promoter sequence is capable of directing the expression of a functional gene in vivo, transgenes containing 114 base pairs of the adipsin 5' flanking region were tested in mice.

The vector was prepared for microinjection into mouse eggs by restricting the vector with NdeI and PvuI. A 3 kb NdeI-PvuI fragment was then separated from the bulk plasmid fragments on an agarose gel and used for injection into eggs. Swiss Webster one-cell zygotes were injected as in Example 3.

Two strains of transgenic mice were generated (114ADN CAT 3 and 114ADN CAT 13). Two male offspring were sacrificed at 1–2 months of age and CAT assays conducted on tissue extracts, as previously described. The specific activities reported in Table 4 below represent the average of the two animals from each strain.

TABLE 4

| Tissue | Specific Activity (cpm/mg/min) | |
|---|---|---|
| | 114adnCAT 3 | 114adnCAT 13 |
| Liver | 0.36 | 0 |
| Salivary Gland | 0.4 | 0 |
| Spleen | 1.1 | 1.2 |
| Kidney | 0 | not done |
| Thymus | 2.0 | 8.5 |
| Brown Fat | 12.4 | not done |
| White Fat | 38.1 | 11.6 |

The results demonstrate that the sequence comprising −114 to +35 of the murine adipsin gene is sufficient to direct the fat specific expression of a heterologous gene in vivo.

The sequence of the 149 bp adipsin promoter, which has previously been published in connection with the cloning of the adipsin gene, is set forth in SEQ ID NO: 2. Larger sequences, which contain this minimal promoter together with additional DNA from the 5' flanking region of the adipsin gene, will also be useful in accordance with the present invention.

EXAMPLE 7

This Example describes the construction of a transgenic promoter vector (TAP), including the 518 bp enhancer sequence and minimal aP2 promoter, which is useful in generating transgenic animals in accordance with the present invention.

| −4.9kb | −5.4kb/−63bp | +21 |
|---|---|---|
| Cloning The Promoter 5' XbaI . . . | EcoRI/HindIII . . . | PstI |

The −5.4 kb to −4.9 kb EcoRI to XbaI fragment of the murine aP2 gene was subcloned into pBS, to yield plasmid 518pBS. 518pBS was then cut with EcoRI, filled in with Klenow, then cut with XbaI and the 518 bp insert prepared for cloning.

−63aP2CAT, described in Example 1, was cut with HindIII, filled in with Klenow, then cut with PstI and an 84 bp fragment prepared.

The commercially available vector, bluescript SKII+ (Strategene, La Jolla, Calif.), was cut with XbaI and PstI and the appropriate fragment isolated.

The DNA from each of the foregoing steps was then ligated in accordance with conventional techniques.

Cloning The Terminator

The 800 bp SV40 small t intron and polyadenylation site from the plasmid pETGL was removed from the vector by BglII and BamHI digestion. The 800 bp fragment was then ligated into BamHI cut pBS+ and a clone in the proper orientation was isolated. (pET$_{GL}$ was generated in our laboratory; however vectors containing the SV40 small t intron and polyadenylation signal are readily available to persons skilled in the art and can alternatively be employed).

Final Construction of TAP

The terminator clone was cleaved with KpnI and XbaI and the 800 bp fragment isolated. The promoter clone was cleaved with KpnI and XbaI and the 3.6 kb vector isolated and prepared for cloning. The thus prepared fragments were then ligated.

A schematic map of the TAP vector is illustrated in FIG. 7.

EXAMPLE 8

This example describes the procedure for preparing a recombinant DNA sequence, TAP-MYOD, in accordance with the present invention and also describes how to use the recombinant sequence in the generation of transgenic mice which are leaner than nontransgenic controls which lack the transgene.

Preparation Of Constructs

Mouse MYOD cDNA is isolated as a 0.9 kb HindIII to EcoRI restriction fragment from a vector available from Harold Weintraub, Fred Hutchinson Cancer Center, Seattle, Wash. The cDNA sequence for the mouse MYOD gene was presented in Davis et al., Cell, 51:987–1000 (1987). This fragment contains the entire MYOD coding sequence. The TAP aP2 promoter vector obtained in accordance with Example 7 is then cleaved with EcoRI and HindIII and the fragment containing MYOD is ligated into the digested TAP vector, to yield a plasmid which contains the aP2 enhancer/basal promoter upstream of the cDNA sequence for MYOD (TAP-MYOD). A schematic map of TAP-MYOD is provided in FIG. 8.

Generation Of Transgenic Mice

The TAP-MYOD construct is prepared for microinjection by NotI and BamHI digestion. A 2.5 kb fragment containing the recombinant aP2MYOD sequence is then isolated and used for microinjection. About 125 eggs are microinjected and replaced into pseudopregnant mice.

Tail blots of the pups are performed and probed with radioactively labeled MYOD cDNA probes, thereby identifying the pups which contain the MYOD sequences. The transgenes are detected by Southern blotting of HindIII and EcoRI digested DNA, in accordance with the procedure described by Hogan et al., Manipulating the Mouse Embryo, Cold Spring Harbor Press (1988). RNA is isolated from fat pads and subjected to Northern blot analysis to test for expression of the MYOD sequences in adipose tissue.

The pups are maintained on a diet of standard laboratory feed after weaning and growth and weight charts are kept on the transgenic animals and age and sex matched non-transgenic controls.

The G0 progeny are mated at six weeks of age to produce a G1 generation. The G1 generation progeny are tested for the presence of the MYOD transgene, as described above and growth and weight charts maintained. Transgenic animals of the G1 generation which express the transgene are sacrificed at about two to three months of age and fat pads, including gonadal, peri-adrenal, subcutaneous and abdominal are removed, weighed and measured to determine the effect of expression of the transgene in adipose tissue.

The mice that carry the MYOD transgene are leaner than the age and sex matched non-transgenic controls.

EXAMPLE 9

This example describes the procedure for preparing a recombinant DNA sequence, TAP-α2-adrenergic, in accordance with the present invention, and also describes how to use the recombinant sequence in the generation of transgenic mice.

Preparation Of Constructs

The α2-adrenergic receptor DNA is isolated as a 1.5 kb NcoI and HindIII restriction of the human genomic clone. The α2 adrenergic receptor DNA is derived from the clone described by Kobilka et al., Science, 238:650 (1987) and is available from Robert Lefkowitz, Duke University Medical School, (Durham, N.C.). The 1.5 bp α2 adrenergic restriction fragment which is isolated contains the entire intronless gene encoding α2 adrenergic. An adaptor oligonucleotide is used to recreate some of the non-coding leader sequence of the α2 adrenergic receptor mRNA and also to join the NcoI site into the PstI site of TAP. The oligomers used are as follows:

---
5' CAT GGG CGC AAA GCT GCC CTG CA 3'
5' GGG CAG CTT TCG GCC 3'
---

The TAP vector, obtained in accordance with Example 7, is then cleaved with PstI and HindIII and the vector isolated. To construct the final vector, the 1.5 kb NcoI and HindIII restriction fragment, oligomers and digested TAP are ligated together to obtain the TAP-α2 adrenergic construct.

A schematic map of the TAP-α2 adrenergic construct is provided in FIG. 9.

Generation Of Transgenic Mice

The TAP-α2 adrenergic receptor construct is prepared for microinjection by digesting with NotI and BamHI and isolating a 3.0 kb fragment. Two hundred ninety-seven eggs are implanted into pseudopregnant mice as described.

The eighty pups that are born are tested for the presence of the α2 adrenergic transgene by conducting an analysis of genomic DNA. Genomic DNA is prepared and the DNA restricted with XbaI, run on 0.8% agarose gels, Southern blotted and probed with α2 adrenergic radioactively labeled cDNA, thereby identifying the pups which contain the α2 adrenergic sequences. A unique 2.1 kb band is detected in six of the animals. RNA is isolated from fat pads and subjected to Northern blot analysis to test for expression of the α2 adrenergic sequences in adipose tissue.

Pups are maintained on a diet of standard laboratory feed after weaning and growth and weight charts are kept on the transgenic animals and age and sex matched non-transgenic controls.

The G0 progeny are mated at six weeks of age to produce a G1 generation. The G1 generation progeny are tested for the presence of the α2 adrenergic sequence, as described above, and growth and weight charts maintained. Transgenic animals of the G1 generation which express the transgene are sacrificed at about two to three months of age and fat pads, including gonadal, peri-adrenal, subcutaneous and abdominal are removed, weighed and measured to determine the effect of expression of the transgene in adipose tissue.

The mice that carry the α2 adrenergic transgene are leaner than the age and sex-matched non-transgenic controls.

EXAMPLE 10

This example describes the experimental protocol for generating a leaner strain of feed animal in accordance with the present invention.

In this example, the linearized 2.5 kb fragment containing the 518aP2-MYOD transgene obtained in accordance with Example 8 was microinjected into zygotes obtained from fertilized pigs.

The procedures for collecting and transferring of zygotes has been described (Hammer et al., Nature, 315: 680– 683 (1985); Wall et al., Biol. of Reprod., 32:645–651 (1985). Briefly, donor gilts will be fed 15 mg altrenogest (17α-allyl-estratriene-4-9-11.17β-ol-3-one; RU-2267; Roussel Uclaf Company, Paris) daily for about 5–9 days beginning on days 12–16 of the oestrous cycle. Gilts will be injected with 1500–2000 IU pregnant mare serum gonadotrophin 24–30 h after the last feeding of altrenogest and with 500 IU human chorionic gonadotrophin (hCG) after an additional 78 h. Gilts are then mated or artificially inseminated 18–36 h after the hCG injection.

Ova are surgically collected from the gilts 57–60 h after the hCG injection by flushing culture medium from the uterotubal junction through the cannulated infundibular end of each oviduct. Ova are collected and maintained in Brinster's medium for ovum culture (BMOC-3; Brinster, 1972) containing 1–5% (w/v) bovine serum albumin (ICN Immuno Biologicals, Lisle, Ill. U.S.A.).

Ova are centrifuged several minutes to stratify the cytoplasm and permit visualization of pronuclei and nuclei by interference-contrast microscopy (Wall et al., 1985). After centrifugation, ova are held for microinjection by a blunt holding pipette (50 μm diameter), while the tip of an injection pipette (1–5 μm diameter) is inserted into one pronucleus of zygotes or each nucleus of two-cell ova. The nuclear structures are injected with about 300 to 500 copies of linear fragment containing the 518aP2-MYOD transgene. After injection, the ova are transferred to recipient gilts by aspirating them into sterile polyethylene tubing, inserting the tubing through the infundibulum and expelling the ova into the lower ampulla.

The offspring will be allowed to develop from these eggs.

At about 4 weeks of age, total nucleic acids are extracted from a piece of the tail of the offspring and used for DNA blot hybridization to determine which of the piglets carry the 518aP2-MYOD transgene. Again, using a radioactively-labelled MYOD cDNA probe, the animals which carry the 518aP2-MYOD transgene are detected by their ability to generate hybridization signals above background. DNA can be further analyzed using an appropriate restriction enzyme(s) and Southern blotting.

The piglets are weaned at about 4 to 6 weeks of age and then housed either separately or in small groups. After weaning, the piglets are maintained on a controlled diet of solid food and water and their growth, weight, and carcass fat composition measured periodically. Non-transgenic age and sex matched piglets serve as controls. Carcass fat thickness is measured on the live animals using real time ultrasound. Ultrasound scanning measurements on the piglets are obtained from a variety of locations in accordance with the conventional wisdom in the art. See, Terry et al., J. Anim. Sci., 67:1279–1284 (1989).

The pigs carrying the transgene exhibit less carcass fat and are leaner than the controls. Maximal expression of the MYOD transgene is in adipose tissue.

From the above description, it is apparent that the objects of the present invention can be readily achieved. While only certain embodiments have been set forth, alternative embodiments and various modifications will be apparent from the above descriptions to those skilled in the art. For example, other adipose specific control sequences may be obtained from other adipose differentiation-linked genes and/or other structural genes exhibiting an effect on adipose tissue metabolism may be employed. These and other alternatives are considered equivalents and within the spirit and scope of the present invention.

SEQUENCE LISTING ( 1 ) GENERAL INFORMATION:

( i i i ) NUMBER OF SEQUENCES: 16

( 2 ) INFORMATION FOR SEQ ID NO:1:

( i ) SEQUENCE CHARACTERISTICS:
        ( A ) LENGTH: 518 base pairs
        ( B ) TYPE: nucleic acid
        ( C ) STRANDEDNESS: double
        ( D ) TOPOLOGY: linear ( i i ) MOLECULE TYPE: genomic DNA ( i i i ) HYPOTHETICAL: no ( i v ) ANTI-SENSE: no ( v i ) ORIGINAL SOURCE:
        ( A ) ORGANISM: Mus musculus
        ( B ) STRAIN: Swiss Webster
        ( D ) DEVELOPMENTAL STAGE: embryonic
        ( F ) TISSUE TYPE: embryonic fibroblast
        ( G ) CELL TYPE: fibroblast
        ( H ) CELL LINE: 3T3-F442A ( v i i ) IMMEDIATE SOURCE:
        ( A ) LIBRARY: genomic
        ( B ) CLONE: aP2911

( x i ) SEQUENCE DESCRIPTION: SEQ ID NO:1:

```
GAATTCCAGC AGGAATCAGG TAGCTGGAGA ATCGCACAGA                    40
GCCATGCGAT TCTTGGCAAG CCATGCGACA AAGGCAGAAA                    80
TGCACATTTC ACCCAGAGAG AAGGGATTGA TGTCAGCAGG                   120
AAGTCACCAC CCAGAGAGCA AATGGAGTTC CCAGATGCCT                   160
GACATTTGCC TTCTTACTGG ATCAGAGTTC ACTAGTGGAA                   200
GTGTCACAGC CCAAACACTC CCCCAAAGCT CAGCCCTTCC                   240
TTGCCTTGTA ACAATCAAGC CGCTCCTGGA TGAACTGCTC                   280
CGCCCTCTGT CTCTTTGGCA GGGTTGGAGC CCACTGTGGC                   320
CTGAGCGACT TCTATGGCTC CCTTTTCTGT GATTTTCATG                   360
GTTTCTGAGC TCTTTTCCCC CGCTTTATGA TTTTCTCTTT                   400
TTGTCTCTCT CTTGCTAAAC CTCCTTCGTA TATATGCCCT                   440
CTCAGGTTTC ATTTCTGAAT CATCTACTGT GAACTATTCC                   480
CATTGTTTGC CAGAAGCCCC CTGGTTCTTC CTTCTAGA                     518
```

( 2 ) INFORMATION FOR SEQ ID NO:2:

( i ) SEQUENCE CHARACTERISTICS:
        ( A ) LENGTH: 149 nucleotides
        ( B ) TYPE: nucleic acid
        ( C ) STRANDEDNESS: double (D) TOPOLOGY: linear (ii) MOLECULE TYPE: genomic DNA (iii) HYPOTHETICAL: no (vi) ORIGINAL SOURCE:
  (A) ORGANISM: Mus musculus
  (B) STRAIN: Swiss Webster
  (D) DEVELOPMENTAL STAGE: embryonic
  (F) TISSUE TYPE: embryonic fibroblast
  (G) CELL TYPE: fibroblast
  (H) CELL LINE: 3T3-F442A (vii) IMMEDIATE SOURCE:
  (A) LIBRARY: genomic
  (B) CLONE: lambda adipsin (x) PUBLICATION INFORMATION:
  (A) AUTHORS: HUNT, CLAYTON R.
        RO, JASON H.S.
        DOBSON, DEBORAH E.
        MIN, HYE YEONG
        SPIEGELMAN, BRUCE M.
  (B) TITLE: Adipocyte P2 Gene: Developmental expression
        and homology of 5'flanking sequences among fat
        cell- specific genes.
  (C) JOURNAL: Proc. Natl. Acad. Sci.
  (D) VOLUME: 83
  (F) PAGES: 3786-3790
  (G) DATE: 00-JUN-1986
  (K) RELEVANT RESIDUES IN SEQ ID NO:2:FROM 1 to 149

(x) PUBLICATION INFORMATION:
  (A) AUTHORS: MIN, HYE YEONG
        SPIEGELMAN, BRUCE M.
  (B) TITLE: Adipsin, the adipocyte serine protease
  (C) JOURNAL: Nucleic Acids Research
  (D) VOLUME: 14
  (E) ISSUE: 22
  (F) PAGES: 8879-8892
  (G) DATE: 1986
  (K) RELEVANT RESIDUES IN SEQ ID NO:2: From 1 to 149

(xi) SEQUENCE DESCRIPTION: SEQ ID NO:2:

```
GGGCTGACAC  ACCGAAAGTG  CAGACTCCCC  TTCCCTAGTT                    40

GGTTTTCTGC  CCACCAGGCA  AGGGGCAGGA  GGTAAGAGGC                    80

AGGAGTCCAT  AAAACAGCCC  TGAGAGCCTG  CTGGGTCAGT                   120

GCCTGCTGTC  AGA ATG CAC AGC TCC GTG T                            149
```

(2) INFORMATION FOR SEQ ID NO:3:

(i) SEQUENCE CHARACTERISTICS:
  (A) LENGTH: 20 nucleotides
  (B) TYPE: nucleic acid
  (C) STRANDEDNESS: single
  (D) TOPOLOGY: linear (ii) MOLECULE TYPE: genomic DNA (iii) HYPOTHETICAL: no (iv) ANTI-SENSE: no (vi) ORIGINAL SOURCE:
  (A) ORGANISM: Simian Virus 40

(x) PUBLICATION INFORMATION:
  (A) AUTHORS: REDDY, V.B.
        THIMMAPPAYA, B.
        DAHR, R.
        SUBRAMANIAN, K.N.
        ZAIN, S.
        PAN, J.

GHOSH, P.K.
SELMA, M.L.
WEISSMAN, S.M.
( C ) JOURNAL: Science
( D ) VOLUME: 200
( F ) PAGES: 494-502
( G ) DATE: 00-00-1978
( K ) RELEVANT RESIDUES IN SEQ ID NO:3: FROM 1 to 20

( x i ) SEQUENCE DESCRIPTION: SEQ ID NO:3:

GACACTCTAT GCCTGTGTGG 20

( 2 ) INFORMATION FOR SEQ ID NO:4:

( i ) SEQUENCE CHARACTERISTICS:
( A ) LENGTH: 20 nucleotides
( B ) TYPE: nucleic acid
( C ) STRANDEDNESS: single
( D ) TOPOLOGY: linear ( i i ) MOLECULE TYPE: genomic DNA ( i i i ) HYPOTHETICAL: no ( i v ) ANTI-SENSE: no ( v i ) ORIGINAL SOURCE:
( A ) ORGANISM: Simian virus 40

( x ) PUBLICATION INFORMATION:
( A ) AUTHORS: REDDY, V.B.
THIMMAPPAYA, B.
DAHR, R.
SUBRAMANIAN, K.N.
ZAIN, S.
PAN, J.
GHOSH, P.K.
SELMA, M.L.
WEISSMAN, S.M.
( C ) JOURNAL: Science
( D ) VOLUME: 200
( F ) PAGES: 494-502
( G ) DATE: 00-00-1978
( K ) RELEVANT RESIDUES IN SEQ ID NO:4: FROM 1 to 20

( x i ) SEQUENCE DESCRIPTION: SEQ ID NO:4

CACACAGTCG TCATCGGAGT 20

( 2 ) INFORMATION FOR SEQ ID NO:5:

( i ) SEQUENCE CHARACTERISTICS:
( A ) LENGTH: 25 base pairs
( B ) TYPE: nucleic acid
( C ) STRANDEDNESS: double
( D ) TOPOLOGY: linear ( i i ) MOLECULE TYPE: genomic DNA ( i i i ) HYPOTHETICAL: no ( i v ) ANTI-SENSE: no ( v i ) ORIGINAL SOURCE:
( A ) ORGANISM: Mus musculus
( B ) STRAIN: Swiss Webster
( D ) DEVELOPMENTAL STAGE: embryonic
( F ) TISSUE TYPE: embryonic fibroblast
( G ) CELL TYPE: fibroblast
( H ) CELL LINE: 3T3-F442A ( v i i ) IMMEDIATE SOURCE:
( A ) LIBRARY: genomic
( B ) CLONE: aP2911

( i x ) FEATURE:

(A) NAME/KEY: regulatory element; identified herein as ARE2
(B) LOCATION: 8 to 18
(C) IDENTIFICATION METHOD: DNase I protection experiments
    and gel mobility shift assays.
(D) OTHER INFORMATION: Nucleotides 8 to 18 of SEQ ID NO 5
    correspond to nucleotides 123 to 133 of the 518 bp
    enhancer in SEQ ID NO 1 and contain a protein binding
    site for a factor in nuclear extract from preadipocytes
    and adipocytes.

(x) PUBLICATION INFORMATION:
    (A) AUTHORS: GRAVES, REED A.
        TONTONOZ, PETER
        SPEIGELMAN, BRUCE M.
    (B) TITLE: Analysis of a Tissue- Specific Enhancer: ARF6
        Regulated Adipogenic Gene Expression
    (C) JOURNAL: Molecular and Cellular Biology
    (D) VOLUME: 12
    (F) PAGES: 1202-1208
    (G) DATE: 00-MAR-1992
    (K) RELEVANT RESIDUES IN SEQ ID NO:5: FROM 1 to 25

(x i) SEQUENCE DESCRIPTION: SEQ ID NO:5:

GCAGGAAGTC ACCACCCAGA GAGCA                          25

(2) INFORMATION FOR SEQ ID NO:6:

(i) SEQUENCE CHARACTERISTICS:
        (A) LENGTH: 25 base pairs
        (B) TYPE: nucleic acid
        (C) STRANDEDNESS: double
        (D) TOPOLOGY: linear (i i) MOLECULE TYPE: genomic DNA (i i i) HYPOTHETICAL: no (i v) ANTI-SENSE: no (v i) ORIGINAL SOURCE:
        (A) ORGANISM: Mus musculus
        (B) STRAIN: Swiss Webster
        (D) DEVELOPMENTAL STAGE: embryonic
        (F) TISSUE TYPE: embryonic fibroblast
        (G) CELL TYPE: fibroblast
        (H) CELL LINE: 3T3-F442A (v i i) IMMEDIATE SOURCE:
        (A) LIBRARY: genomic
        (B) CLONE: aP2911

(i x) FEATURE:
        (A) NAME/KEY: regulatory element; identified herein as ARE4
        (B) LOCATION: 8 to 18
        (C) IDENTIFICATION METHOD: DNase I protection experiments
            and
            gel mobility shift assays.
        (D) OTHER INFORMATION: Nucleotides 8 to 18 of SEQ ID NO 6
            correspond to nucleotides 203 to 213 of the 518 bp
            enhancer in SEQ ID NO 1; this sequence appears to bind
            the same nuclear factor as ARE2.

(x) PUBLICATION INFORMATION:
        (A) AUTHORS: GRAVES, REED A.
            TONTONOZ, PETER
            SPEIGELMAN, BRUCE M.
        (B) TITLE: Analysis of a Tissue- Specific Enhancer: ARF6
            Regulated Adipogenic Gene Expression
        (C) JOURNAL: Molecular and Cellular Biology
        (D) VOLUME: 12
        (F) PAGES: 1202-1208
        (G) DATE: 00-MAR-1992
        (K) RELEVANT RESIDUES IN SEQ ID NO:6: FROM 1 to 25

(x i) SEQUENCE DESCRIPTION: SEQ ID NO:6:

TGGAAGTGTC ACAGCCCAAA CACTC                          25

( 2 ) INFORMATION FOR SEQ ID NO:7:

( i ) SEQUENCE CHARACTERISTICS:
  ( A ) LENGTH: 25 base pairs
  ( B ) TYPE: nucleic acid
  ( C ) STRANDEDNESS: double
  ( D ) TOPOLOGY: linear ( i i ) MOLECULE TYPE: mutated genomic DNA ( i i i ) HYPOTHETICAL: no ( i v ) ANTI-SENSE: no ( v i ) ORIGINAL SOURCE:
  ( A ) ORGANISM: Mus musculus
  ( B ) STRAIN: Swiss Webster
  ( D ) DEVELOPMENTAL STAGE: embryonic
  ( F ) TISSUE TYPE: embryonic fibroblast
  ( G ) CELL TYPE: fibroblast
  ( H ) CELL LINE: 3T3-F442A ( v i i ) IMMEDIATE SOURCE:
  ( A ) LIBRARY: genomic
  ( B ) CLONE: aP2911

( x ) PUBLICATION INFORMATION:
  ( A ) AUTHORS: GRAVES, REED A.
   TONTONOZ, PETER
   SPEIGELMAN, BRUCE M.
  ( B ) TITLE: Analysis of a Tissue- Specific Enhancer: ARF6
   Regulated Adipogenic Gene Expression
  ( C ) JOURNAL: Molecular and Cellular Biology
  ( D ) VOLUME: 12
  ( F ) PAGES: 1202-1208
  ( G ) DATE: 00-MAR-1992
  ( K ) RELEVANT RESIDUES IN SEQ ID NO:7: FROM 1 to 25

( x i ) SEQUENCE DESCRIPTION: SEQ ID NO:7:

GCAGGAAGTG TAAGCCCAGA GAGCA              25

( 2 ) INFORMATION FOR SEQ ID NO:8:

( i ) SEQUENCE CHARACTERISTICS:
  ( A ) LENGTH: 25 base pairs
  ( B ) TYPE: nucleic acid
  ( C ) STRANDEDNESS: double
  ( D ) TOPOLOGY: linear ( i i ) MOLECULE TYPE: genomic DNA ( i i i ) HYPOTHETICAL: no ( i v ) ANTI-SENSE: no ( v i ) ORIGINAL SOURCE:
  ( A ) ORGANISM: Mus musculus
  ( B ) STRAIN: Swiss Webster
  ( D ) DEVELOPMENTAL STAGE: embryonic
  ( F ) TISSUE TYPE: embryonic fibroblast
  ( G ) CELL TYPE: fibroblast
  ( H ) CELL LINE: 3T3-F442A ( v i i ) IMMEDIATE SOURCE:
  ( A ) LIBRARY: genomic
  ( B ) CLONE: aP2911

( i x ) FEATURE:
  ( A ) NAME/KEY: aP2 regulatory element; identified herein as
   ARE6
  ( B ) LOCATION: 8 to 19
  ( C ) IDENTIFICATION METHOD: multimerization of known sequence
   in pSVKS1- CAT vector; transfection assays; gel mobility
   shift
   assays.

(D) OTHER INFORMATION: Nucleotides 8 to 19 of SEQ ID NO 6
correspond to nucleotides 93 to 104 of the 518 bp
enhancer in SEQ ID NO 1; this sequence binds a protein
factor present in the nuclear extract of differentiated
adipocytes.

(x) PUBLICATION INFORMATION:
(A) AUTHORS: GRAVES, REED A.
TONTONOZ, PETER
SPEIGELMAN, BRUCE M.
(B) TITLE: Analysis of a Tissue- Specific Enhancer: ARF6
Regulated Adipogenic Gene Expression
(C) JOURNAL: Molecular and Cellular Biology
(D) VOLUME: 12
(F) PAGES: 1202-1208
(G) DATE: 00-MAR-1992
(K) RELEVANT RESIDUES IN SEQ ID NO:8: FROM 1 to 25

(x i) SEQUENCE DESCRIPTION: SEQ ID NO:8:

ATTTCACCCA GAGAGAAGGG ATTGa 25

(2) INFORMATION FOR SEQ ID NO:9:

(i) SEQUENCE CHARACTERISTICS:
(A) LENGTH: 25 base pairs
(B) TYPE: nucleic acid
(C) STRANDEDNESS: double
(D) TOPOLOGY: linear (i i) MOLECULE TYPE: genomic DNA (i i i) HYPOTHETICAL: no (i v) ANTI-SENSE:

(v i) ORIGINAL SOURCE:
(A) ORGANISM: Mus musculus
(B) STRAIN: Swiss Webster
(D) DEVELOPMENTAL STAGE: embryonic
(F) TISSUE TYPE: embryonic fibroblast
(G) CELL TYPE: fibroblast
(H) CELL LINE: 3T3-F442A (v i i) IMMEDIATE SOURCE:
(A) LIBRARY: genomic
(B) CLONE: aP2911

(i x) FEATURE:
(A) NAME/KEY: aP2 regulatory element; identified herein as
ARE7
(B) LOCATION: 8 to 19
(C) IDENTIFICATION METHOD: multimerization of known sequence
in pSVKS1- CAT vector; tranfection assays; gel mobility
shift assays.
(D) OTHER INFORMATION: Nucleotides 8 to 19 of SEQ ID NO 6
are complementary to nucleotides 180 to 169 on the
non-coding strand of the 518 base pair enhancer in
SEQ ID NO 1 herein; this sequence appears to bind the
same protein factor as ARE6.

(x) PUBLICATION INFORMATION:
(A) AUTHORS: GRAVES, REED A.
TONTONOZ, PETER
SPEIGELMAN, BRUCE M.
(B) TITLE: Analysis of a Tissue- Specific Enhancer: ARF6
Regulated Adipogenic Gene Expression
(C) JOURNAL: Molecular and Cellular Biology
(D) VOLUME: 12
(F) PAGES: 1202-1208
(G) DATE: 00-MAR-1992
(K) RELEVANT RESIDUES IN SEQ ID NO:9: FROM 1 to 25

(x i) SEQUENCE DESCRIPTION: SEQ ID NO:9:

CTCTGATCCA GTAAGAAGGC AAATG 25

( 2 ) INFORMATION FOR SEQ ID NO:10:

( i ) SEQUENCE CHARACTERISTICS:
        ( A ) LENGTH: 25 base pairs
        ( B ) TYPE: nucleic acid
        ( C ) STRANDEDNESS: double
        ( D ) TOPOLOGY: linear ( i i ) MOLECULE TYPE: mutated genomic DNA ( i i i ) HYPOTHETICAL: no ( i v ) ANTI-SENSE: no ( v i ) ORIGINAL SOURCE:
        ( A ) ORGANISM: Mus musculus
        ( B ) STRAIN: Swiss Webster
        ( D ) DEVELOPMENTAL STAGE: embryonic
        ( F ) TISSUE TYPE: embryonic fibroblast
        ( G ) CELL TYPE: fibroblast
        ( H ) CELL LINE: 3T3-F442A ( v i i ) IMMEDIATE SOURCE:
        ( A ) LIBRARY: genomic
        ( B ) CLONE: aP2911

( x ) PUBLICATION INFORMATION:
        ( A ) AUTHORS: GRAVES, REED A.
                TONTONOZ, PETER
                SPEIGELMAN, BRUCE M.
        ( B ) TITLE: Analysis of a Tissue- Specific Enhancer: ARF6
                Regulated Adipogenic Gene Expression
        ( C ) JOURNAL: Molecular and Cellular Biology
        ( D ) VOLUME: 12
        ( F ) PAGES: 1202-1208
        ( G ) DATE: 00-MAR-1992
        ( K ) RELEVANT RESIDUES IN SEQ ID NO:10: FROM 1 to 25

( x i ) SEQUENCE DESCRIPTION: SEQ ID NO:10:

```
ATTTCACCCA TCTAGAAGGG ATTGA                                    25
```

( 2 ) INFORMATION FOR SEQ ID NO:11:

( i ) SEQUENCE CHARACTERISTICS:
        ( A ) LENGTH: 25 base pairs
        ( B ) TYPE: nucleic acid
        ( C ) STRANDEDNESS: double
        ( D ) TOPOLOGY: linear ( i i ) MOLECULE TYPE: mutated genomic DNA ( i i i ) HYPOTHETICAL: no ( i v ) ANTI-SENSE: no ( v i ) ORIGINAL SOURCE:
        ( A ) ORGANISM: Mus musculus
        ( B ) STRAIN: Swiss Webster
        ( D ) DEVELOPMENTAL STAGE: embryonic
        ( F ) TISSUE TYPE: embryonic fibroblast
        ( G ) CELL TYPE: fibroblast
        ( H ) CELL LINE: 3T3-F442A ( v i i ) IMMEDIATE SOURCE:
        ( A ) LIBRARY: genomic
        ( B ) CLONE: aP2911

( x ) PUBLICATION INFORMATION:
        ( A ) AUTHORS: GRAVES, REED A.
                TONTONOZ, PETER
                SPEIGELMAN, BRUCE M.
        ( B ) TITLE: Analysis of a Tissue- Specific Enhancer: ARF6
                Regulated Adipogenic Gene Expression
        ( C ) JOURNAL: Molecular and Cellular Biology
        ( D ) VOLUME: 12
        ( F ) PAGES: 1202-1208
        ( G ) DATE: 00-MAR-1992

( K ) RELEVANT RESIDUES IN SEQ ID NO:11: FROM 1 to 25

( x i ) SEQUENCE DESCRIPTION: SEQ ID NO:11:

ATTTCCTGCA GAGAGAAGGG ATTGA                25

( 2 ) INFORMATION FOR SEQ ID NO:12:

( i ) SEQUENCE CHARACTERISTICS:
        ( A ) LENGTH: 33 base pairs
        ( B ) TYPE: nucleic acid
        ( C ) STRANDEDNESS: double
        ( D ) TOPOLOGY: linear ( i i ) MOLECULE TYPE: genomic DNA ( i i i ) HYPOTHETICAL: no ( i v ) ANTI-SENSE: no ( v i ) ORIGINAL SOURCE:
        ( A ) ORGANISM: Mus musculus
        ( B ) STRAIN: Swiss Webster
        ( D ) DEVELOPMENTAL STAGE: embryonic
        ( F ) TISSUE TYPE: embryonic fibroblast
        ( G ) CELL TYPE: fibroblast
        ( H ) CELL LINE: 3T3-F442A ( v i i ) IMMEDIATE SOURCE:
        ( A ) LIBRARY: genomic
        ( B ) CLONE: aP2911

( i x ) FEATURE:
        ( A ) NAME/KEY: ARE6-containing sequence.
        ( B ) LOCATION: 17 to 28
        ( D ) OTHER INFORMATION: This nucleotide sequence includes
            the aP2 regulatory element identified herein as ARE6.
            The sequence encompasses the ARE6-containing nucleotide
            sequence of SEQ ID NO 8 herein and includes an additional
            nine nucleotides, "TCGGCGCAC" of 5' flanking region of
            the mouse aP2 gene.

( x ) PUBLICATION INFORMATION:
        ( A ) AUTHORS: GRAVES, REED A.
            TONTONOZ, PETER
            SPEIGELMAN, BRUCE M.
        ( B ) TITLE: Analysis of a Tissue- Specific Enhancer: ARF6
            Regulated Adipogenic Gene Expression
        ( C ) JOURNAL: Molecular and Cellular Biology
        ( D ) VOLUME: 12
        ( F ) PAGES: 1202-1208
        ( G ) DATE: 00-MAR-1992

( x i ) SEQUENCE DESCRIPTION: SEQ ID NO:12:

TCGGCGCACA TTTCACCCAG AGAGAAGGGA TTG                33

( 2 ) INFORMATION FOR SEQ ID NO:13:

( i ) SEQUENCE CHARACTERISTICS:
        ( A ) LENGTH: 28 base pairs
        ( B ) TYPE: nucleic acid
        ( C ) STRANDEDNESS: double
        ( D ) TOPOLOGY: linear ( i i ) MOLECULE TYPE: mutated genomic DNA ( i i i ) HYPOTHETICAL: no ( i v ) ANTI-SENSE: no ( v i ) ORIGINAL SOURCE:
        ( A ) ORGANISM: Mus musculus
        ( B ) STRAIN: Swiss Webster
        ( D ) DEVELOPMENTAL STAGE: embryonic
        ( F ) TISSUE TYPE: embryonic fibroblast
        ( G ) CELL TYPE: fibroblast -continued

```
            ( H ) CELL LINE: 3T3-F442A ( v i i ) IMMEDIATE SOURCE:
            ( A ) LIBRARY: genomic
            ( B ) CLONE: aP2911

( i x ) FEATURE:
            ( A ) NAME/KEY: ARE6- containing nucleotide sequence mutated
                    in the ARE6 site sequence.
            ( B ) LOCATION: 12 - 23
            ( D ) OTHER INFORMATION: the oligonucleotide sequence
                    corresponds to the mutated oligonucleotide sequence set
                    forth in SEQ ID NO 10 herein, except that the first
                    four nucleotides of SEQ ID NO 13 are not shown in
                    SEQ ID NO 10 and SEQ ID NO 10 shows an additional
                    nucleotide, "A", at the 3'end of the sequence.

( x ) PUBLICATION INFORMATION:
            ( A ) AUTHORS: GRAVES, REED A.
                    TONTONOZ, PETER
                    SPEIGELMAN, BRUCE M.
            ( B ) TITLE: Analysis of a Tissue- Specific Enhancer: ARF6
                    Regulated Adipogenic Gene Expression
            ( C ) JOURNAL: Molecular and Cellular Biology
            ( D ) VOLUME: 12
            ( F ) PAGES: 1202-1208
            ( G ) DATE: 00-MAR-1992

( x i ) SEQUENCE DESCRIPTION: SEQ ID NO:13:

GCACATTTCA CCCATCTAGA AGGGATTG                                                  2 8

( 2 ) INFORMATION FOR SEQ ID NO:14:

( i ) SEQUENCE CHARACTERISTICS:
            ( A ) LENGTH: 24 base pairs
            ( B ) TYPE: nucleic acid
            ( C ) STRANDEDNESS: double
            ( D ) TOPOLOGY: linear ( i i ) MOLECULE TYPE: mutated genomic DNA ( i i i ) HYPOTHETICAL: no ( i v ) ANTI-SENSE: no ( v i ) ORIGINAL SOURCE:
            ( A ) ORGANISM: Mus musculus
            ( B ) STRAIN: Swiss Webster
            ( D ) DEVELOPMENTAL STAGE: embryonic
            ( F ) TISSUE TYPE: embryonic fibroblast
            ( G ) CELL TYPE: fibroblast
            ( H ) CELL LINE: 3T3-F442A ( v i i ) IMMEDIATE SOURCE:
            ( A ) LIBRARY: genomic
            ( B ) CLONE: aP2911

( i x ) FEATURE:
            ( A ) NAME/KEY: ARE6-containing nucleotide sequence mutated in
                    the ARE6 site.
            ( B ) LOCATION: 12 - 23
            ( D ) OTHER INFORMATION: This oligonucleotide corresponds to
                    the sequence in SEQ ID NO 11, which depicts an
                    ARE6- containing oligonucleotide with a mutation in the
                    ARE6 site, except that the nucleotide sequence of
                    SEQ ID NO 11 does not show the first 4 nucleotides of
                    SEQ ID NO 14 and includes five additional nucleotides,
                    " ATTGA"at the 3'end of the sequence.

( x ) PUBLICATION INFORMATION:
            ( A ) AUTHORS: GRAVES, REED A.
                    TONTONOZ, PETER
                    SPEIGELMAN, BRUCE M.
            ( B ) TITLE: Analysis of a Tissue- Specific Enhancer: ARF6
                    Regulated Adipogenic Gene Expression
            ( C ) JOURNAL: Molecular and Cellular Biology
            ( D ) VOLUME: 12
```

-continued ( F ) PAGES: 1202-1208
        ( G ) DATE: 00-MAR-1992

( x i ) SEQUENCE DESCRIPTION: SEQ ID NO:14:

GCACATTTCC TGCAGAGAGA AGGG                                                                      2 4

( 2 ) INFORMATION FOR SEQ ID NO:15:

( i ) SEQUENCE CHARACTERISTICS:
                ( A ) LENGTH: 33 base pairs
                ( B ) TYPE: nucleic acid
                ( C ) STRANDEDNESS: double
                ( D ) TOPOLOGY: linear ( i i ) MOLECULE TYPE: genomic DNA ( i i i ) HYPOTHETICAL: no ( i v ) ANTI-SENSE: no ( v i ) ORIGINAL SOURCE:
                ( A ) ORGANISM: Mus musculus
                ( B ) STRAIN: Swiss Webster
                ( D ) DEVELOPMENTAL STAGE: embryonic
                ( F ) TISSUE TYPE: embryonic fibroblast
                ( G ) CELL TYPE: fibroblast
                ( H ) CELL LINE: 3T3-F442A ( v i i ) IMMEDIATE SOURCE:
                ( A ) LIBRARY: genomic
                ( B ) CLONE: aP2911

( i x ) FEATURE:
                ( A ) NAME/KEY: oligonucleotide containing a regulatory
                        element identified herein as ARE2
                ( B ) LOCATION: 10 - 20
                ( D ) OTHER INFORMATION: Nucleotides 1 to 25 of SEQ ID NO 5
                        correspond to nucleotides 3 to 27 of SEQ ID NO 15.

( x ) PUBLICATION INFORMATION:
                ( A ) AUTHORS: GRAVES, REED A.
                        TONTONOZ, PETER
                        SPEIGELMAN, BRUCE M.
                ( B ) TITLE: Analysis of a Tissue- Specific Enhancer: ARF6
                        Regulated Adipogenic Gene Expression
                ( C ) JOURNAL: Molecular and Cellular Biology
                ( D ) VOLUME: 12
                ( F ) PAGES: 1202-1208
                ( G ) DATE: 00-MAR-1992

( x i ) SEQUENCE DESCRIPTION: SEQ ID NO:15:

CAGCAGGAAG TCACCACCCA GAGAGCAAAT GGA                                                            3 3

( 2 ) INFORMATION FOR SEQ ID NO:16:

( i ) SEQUENCE CHARACTERISTICS:
                ( A ) LENGTH: 41 base pairs
                ( B ) TYPE: nucleic acid
                ( C ) STRANDEDNESS: double
                ( D ) TOPOLOGY: linear ( i i ) MOLECULE TYPE: genomic DNA ( i i i ) HYPOTHETICAL: no ( i v ) ANTI-SENSE:

( v i ) ORIGINAL SOURCE:
                ( A ) ORGANISM: Mus musculus
                ( B ) STRAIN: Swiss Webster
                ( D ) DEVELOPMENTAL STAGE: embryonic
                ( F ) TISSUE TYPE: embryonic fibroblast
                ( G ) CELL TYPE: fibroblast
                ( H ) CELL LINE: 3T3-F442A (vii) IMMEDIATE SOURCE:
    (A) LIBRARY: genomic
    (B) CLONE: aP2911

(ix) FEATURE:
    (A) NAME/KEY: ARE7-containing nucleotide sequence
    (B) LOCATION: 29 - 41
    (D) OTHER INFORMATION: Nucleotides 29 to 41 of SEQ ID NO 16
        are the nucleotides on the coding strand of the mouse
        aP2 gene that are complementary to nucleotides 9 - 19 of
        SEQ ID NO 9, which are on the non-coding strand of the
        mouse aP2 gene.

(x) PUBLICATION INFORMATION:
    (A) AUTHORS: GRAVES, REED A.
        TONTONOZ, PETER
        SPEIGELMAN, BRUCE M.
    (B) TITLE: Analysis of a Tissue- Specific Enhancer: ARF6
        Regulated Adipogenic Gene Expression
    (C) JOURNAL: Molecular and Cellular Biology
    (D) VOLUME: 12
    (F) PAGES: 1202-1208
    (G) DATE: 00-MAR-1992

(xi) SEQUENCE DESCRIPTION: SEQ ID NO:16:

CAAATGGAGT TCCCAGATGC CTGACATTTG CCTTCTTACT G    41

Having described the invention, what is claimed is:

1. A DNA sequence comprising an adipose-specific DNA sequence operatively linked through a functional promoter to a heterologous gene coding for a recombinant protein having either a lipolytic or lipogenic effect on adipose tissue, wherein the adipose-specific DNA sequence comprises an enhancer sequence from the 5' flanking region of the gene encoding murine aP2 lipid binding protein, and wherein the enhancer is normally located about 5.4 kb from the site of transcriptional initiation and is capable of directing fat-specific expression of said heterologous gene in vivo.

2. A DNA sequence according to claim 1, wherein the aP2 enhancer includes the nucleotide sequence set forth in SEQ ID NO:1 or a fragment, genetic variant or deletion thereof which retains the ability to direct fat-specific expression of said heterologous gene specifically in adipose tissue in vivo.

3. A DNA sequence according to claim 2, wherein the functional promoter is a homologous promoter.

4. A DNA sequence according to claim 2, wherein the functional promoter is a heterologous promoter.

5. A murine adipose-specific enhancer element isolated from the 5' flanking region, at about −5.4 kb from the transcription initiation site of transcription of the murine aP2 lipid binding protein gene expressed primarily in differentiated adipocytes, wherein said enhancer element, when operatively linked through a functional promoter to a heterologous DNA sequence coding for a recombinant protein, is capable of directing the expression of the protein specifically in adipose tissue in vivo.

6. A murine adipose-specific enhancer element according to claim 5, wherein the enhancer element has the nucleotide sequence set forth in SEQ ID NO:1 or is a fragment, genetic variant or deletion thereof which retains the ability to direct the expression of a heterologous DNA sequence encoding a recombinant protein in vivo.

7. A DNA sequence according to claim 3, wherein the homologous prompter comprises a minimal promoter from the mouse aP2 gene comprising base pairs −63 to +21 (nucleotides 52–134 of SEQ ID NO. 2.

* * * * *